(12) United States Patent
Krosky et al.

(10) Patent No.: US 9,687,639 B1
(45) Date of Patent: Jun. 27, 2017

(54) MEDICAL TREATMENT

(75) Inventors: Ronald Charles Krosky, Lakewood, OH (US); Brendan Edward Clark, Rocky River, OH (US); Matthew Franklin Clapper, Hudson, OH (US)

(73) Assignees: Ronald Charles Krosky, Rocky River, OH (US); Brendan Edward Clark, Rocky River, OH (US)

( * ) Notice: Subject to any disclaimer, the term of this patent is extended or adjusted under 35 U.S.C. 154(b) by 1752 days.

(21) Appl. No.: 12/816,382

(22) Filed: Jun. 15, 2010

Related U.S. Application Data

(60) Provisional application No. 61/221,086, filed on Jun. 28, 2009.

(51) Int. Cl.
*A61M 31/00* (2006.01)

(52) U.S. Cl.
CPC ... *A61M 31/002* (2013.01); *A61M 2205/3303* (2013.01); *A61M 2210/1042* (2013.01)

(58) Field of Classification Search
CPC ............... A61M 31/00; A61M 31/002; A61M 2205/04; A61M 2205/3303; A61M 2210/1042; A61M 2210/1053; A61M 2210/1057; A61M 2210/106; A61M 2210/1064
USPC ................................................ 604/890.1, 67
See application file for complete search history.

(56) References Cited

U.S. PATENT DOCUMENTS

| | | | |
|---|---|---|---|
| 5,842,975 A | 12/1998 | Illyes et al. | |
| 6,081,786 A | 6/2000 | Barry et al. | |
| 6,126,450 A | 10/2000 | Mukai et al. | |
| 6,188,988 B1 | 2/2001 | Barry et al. | |
| 6,355,623 B2 | 3/2002 | Seidman et al. | |
| 6,680,302 B2 | 1/2004 | Seidman et al. | |
| 6,929,636 B1 | 8/2005 | von Alten | |
| 2001/0001852 A1 | 5/2001 | Rovinelli et al. | |
| 2006/0061472 A1* | 3/2006 | Lovoi et al. | 340/572.1 |
| 2007/0118347 A1 | 5/2007 | Kouchi et al. | |
| 2007/0213659 A1* | 9/2007 | Trovato et al. | 604/67 |
| 2008/0015418 A1 | 1/2008 | Jarrell et al. | |
| 2008/0097733 A1 | 4/2008 | Alsafadi | |
| 2008/0113324 A1 | 5/2008 | Ishii et al. | |
| 2010/0145316 A1 | 6/2010 | Mintchev et al. | |

OTHER PUBLICATIONS

SPICE—Wikipedia, the free encyclopedia, http://en.wikipedia.org/wiki/SPICE, accessed on Jun. 14, 2010, 6 pages.
Microsoft Visio—Wikipedia, the free encyclopedia, http://en.wikipedia.org/wiki/Visio, accessed on Jun. 14, 2010, 4 pages.

* cited by examiner

*Primary Examiner* — Kami A Bosworth

(57) ABSTRACT

Systems, methods, and other embodiments associated with organism medical treatment are described. In one embodiment, a system can comprise a collection component configured to receive a medical control instruction. The medical control instruction can be based, at least in part, on an organism medical information set for an organism. The system can further comprise a regulation component configured to control administration of a treatment to the organism. The regulation component can control the administration of the treatment to the organism based, at least in part, on the medical control instruction.

20 Claims, 20 Drawing Sheets

MEDICAL TREATMENT

CROSS REFERENCE TO RELATED APPLICATIONS

This application claims the benefit of U.S. provisional application Ser. No. 61/221,086 filed on Jun. 28, 2009, which is hereby wholly incorporated by reference.

BACKGROUND

An organism, such as a human being, can include various organs. These organs can perform biological functions in interrelated and/or independent fashions to sustain the organism. In one example functionality, the organism can experience blood flow through a cardiovascular system. The cardiovascular system can include a heart, veins, arteries, and others. In the event that the organism is subject to a disease, such as the cardiovascular system having reduced functionality, then the organism may experience negative effects such as physical pain, permanent loss of functionality, death, and others. In an attempt to stop and/or minimize the negative effects, the organism can experience a medical treatment.

BRIEF DESCRIPTION OF THE FIGURES

The accompanying drawings, which are incorporated in and constitute a part of the detailed description, illustrate various example systems, methods, and other example embodiments of various innovative aspects. These drawings include.

Figure 1:
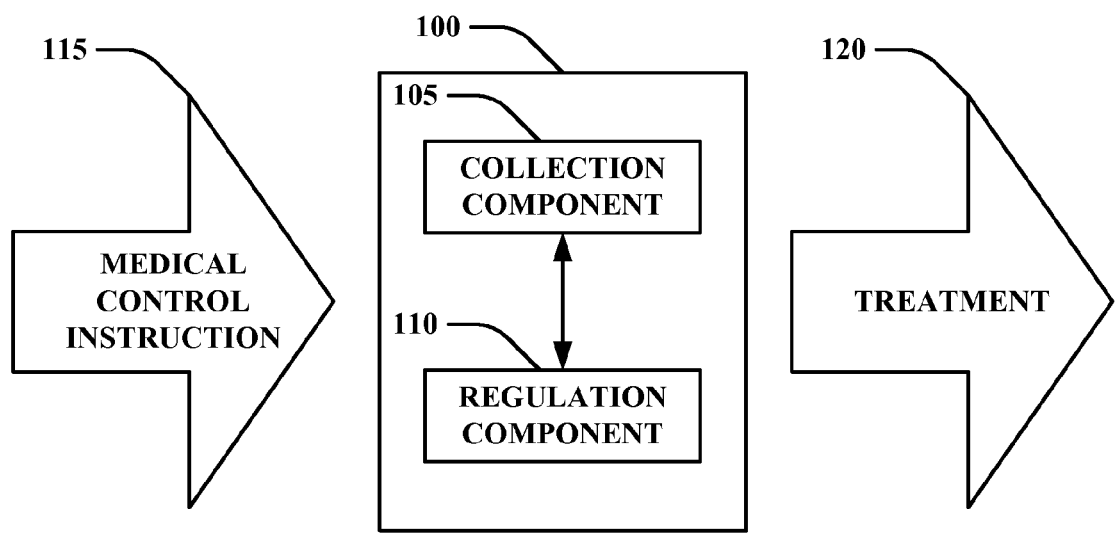
FIG. 1 that illustrates one embodiment of a system that includes a collection component and a regulation component, FIG. 2 that illustrates one embodiment of a system that includes the collection component and the regulation component, FIG. 3 that illustrates one embodiment of a system that includes a release component and a repository, FIG. 4 that illustrates one embodiment of a system that includes a joiner component, a first repository, and a second repository, FIG. 5 that illustrates one embodiment of a system that includes a creation component, FIG. 6 that illustrates one embodiment of a system that includes the collection component and the regulation component, FIG. 7 that illustrates one embodiment of a system that includes an ingestible housing, FIG. 8 that illustrates one embodiment of a system that includes an evaluation component and a decision component, FIG. 9 that illustrates one embodiment of a system that includes a balance component, FIG. 10 that illustrates one embodiment of a system that includes a prediction component, FIG. 11 that illustrates one embodiment of a system that includes a quantity component, FIG. 12 that illustrates one embodiment of a system that includes a generation component and a management component, FIG. 13 that illustrates one embodiment of a method for collecting a housing and controlling a separation, FIG. 14 that illustrates one embodiment of a method for controlling a replacement of a medical component, FIG. 15 that illustrates one embodiment of a method for management of a personal profile, FIG. 16 that illustrates one embodiment of a method for evaluating treatment effectiveness, FIG. 17 that illustrates one embodiment of a method for creating an apparatus for treatment, FIG. 18 that illustrates one embodiment of a method for managing treatment, FIG. 19 that illustrates one embodiment of an example system that can be used in practice of at least one innovative aspect disclosed herein, and FIG. 20 that illustrates one embodiment of an example system that can be used in practice of at least one innovative aspect disclosed herein.

It will be appreciated that illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale. These elements and other variations are considered to be embraced by the general theme of the figures, and it is understood that the drawings are intended to convey the spirit of certain features related to this application, and are by no means regarded as exhaustive or fully inclusive in their representations. Additionally, it is to be appreciated that the designation 'FIG.' represents 'Figure'. In one example, 'FIG. 1' and 'FIG. 1' are referring to the same drawing.

The terms 'may' and 'can' are used to indicate a permitted feature, or alternative embodiments, depending on the context of the description of the feature or embodiments. In one example, a sentence states 'A can be AA' or 'A may be AA'. Thus, in the former case, in one embodiment A is AA, and in another embodiment A is not AA. In the latter case, A may be selected to be AA, or A may be selected not to be AA. However, this is an example of A, and A should not be construed as only being AA. In either case, however, the alternative or permitted embodiments in the written description are not to be construed as injecting ambiguity into the appended claims. Where claim 'x' recites A is AA, for instance, then A is not to be construed as being other than AA for purposes of claim 'x'. This is construction is so despite any permitted or alternative features and embodiments described in the written description.

DETAILED DESCRIPTION

Described herein are example systems, methods, and other embodiments associated with organism medical treatment. Example organisms include humans, mammals, birds, fish, plants, and others. In a conventional setting, an organism becomes sick and can receive a treatment that is generically provided. In one example, a person can have a headache. To alleviate this headache, the person can take an aspirin pill of a set dosage and in taking the pill the person is subjected to the dosage.

A solution employing a pill (or pills) of standardized, fixed dosage can cause a person to become over-medicated or under-medicated. In an example of over-medication, the person can have a small headache that could be treated with a relatively small dosage but receives more medicine than appropriate to alleviate the headache due to the standard, fixed dosages of over the counter aspirin pills. Over-medication can cause a waste of money (e.g., spending more money on medicine than appropriate to alleviate a headache or other ailment), negative health repercussions (e.g., aspirin may cause side effects in a person and more aspirin can cause greater side effects), and other negative repercussions.

In addition to over-medication, under-medication can occur. In one example, a person can take an insufficient dosage to cure the headache. This can cause the person to have to take more pills and take longer for the person to be cured. While a headache can be relatively minor, if in a different example a person suffers from serious pain, then delayed relief can be quite burdensome. In addition, if a medical problem is serious or life-threatening, than under-medication can cause the medical problem to not be cured and ultimately cause permanent injury or death.

Therefore, a device can be used that controls treatment of a disease based on real-time information. In one example, a person can ingest a pill that includes a quantity of medicine stored in a repository, a sensor, and a processor. When the person takes the pill, the pill can determine (e.g., through at least one component of the processor) what medicine to release, what quantity of medicine to release, when to release the medicine, and others.

In one example, the person can suffer from a fever and have a body temperature of 101.6° F. while a normal temperature may be considered 98.6° F. The pill can initially release an amount X of a medicine. In response to this medicine release, the body temperature is 99.6° F. Based on the body temperature being 99.6° F., the pill can release an amount Y of the medicine. In response to this medicine release, the body temperature is 98.6° F. Now that the body temperature is the normal temperature, the pill can stop releasing medicine. The pill can pass through the person, leaving the person without the fever, and without being over- or under-medicated.

While these provide particular aspects of at least one embodiment, other applications involving different features, variations or combinations of aspects will be apparent to those skilled in the art based on the following details relating to the drawings and other portions of this application. Additionally, when a reference is made herein to a person, it is to be appreciated that the reference can be made to an organism.

The following paragraphs include definitions of selected terms discussed at least in the detailed description. The definitions may include examples used to explain features of terms and are not intended to be limiting. In addition, where a singular term is disclosed, it is to be appreciated that plural terms are also covered by the definitions. Conversely, where a plural term is disclosed, it is to be appreciated that a singular term is also covered by the definition.

References to "one embodiment", "an embodiment", "one example", "an example", and so on, indicate that the embodiment(s) or example(s) so described may include a particular feature. The embodiment(s) or example(s) are shown to highlight one feature and no inference should be drawn that every embodiment necessarily includes that feature. Multiple usages of the phrase "in one embodiment" and others do not necessarily refer to the same embodiment; however this term may refer to the same embodiment. It is to be appreciated that multiple examples and/or embodiments may be combined together to form another embodiment.

"Computer-readable medium", as used herein, refers to a medium that stores signals, instructions, and/or data. A computer may access a computer-readable medium and read information stored on the computer-readable medium. In one embodiment, the computer-readable medium stores instruction and the computer can perform those instructions as a method. The computer-readable medium may take forms, including, but not limited to, non-volatile media (e.g., optical disks, magnetic disks, and so on), and volatile media (e.g., semiconductor memories, dynamic memory, and so on). Example forms of a computer-readable medium may include, but are not limited to, a floppy disk, a flexible disk, a hard disk, a magnetic tape, other magnetic medium, an application specific integrated circuit (ASIC), a programmable logic device, a compact disk (CD), other optical medium, a random access memory (RAM), a read only memory (ROM), a memory chip or card, a memory stick, and other media from which a computer, a processor or other electronic device can read.

"Component", "logic", "module", "interface" and the like as used herein, includes but is not limited to hardware, firmware, software stored or in execution on a machine, a routine, a data structure, and/or at least one combination of these (e.g., hardware and software stored). Component, logic, module, and interface may be used interchangeably. A component may be used to perform a function(s) or an action(s), and/or to cause a function or action from another component, method, and/or system. A component may include a software controlled microprocessor, a discrete logic (e.g., ASIC), an analog circuit, a digital circuit, a programmed logic device, a memory device containing instructions, a process running on a processor, a processor, an object, an executable, a thread of execution, a program, a computer and so on. A component may include one or more gates, combinations of gates, or other circuit components. Where multiple components are described, it may be possible to incorporate the multiple components into one physical component. Similarly, where a single component is described, it may be possible to distribute that single component between multiple physical components. In one embodiment, the multiple physical components are distributed among a network. By way of illustration, both/either a controller and/or an application running on a controller can be one or more components.

FIG. 1 illustrates one embodiment of a system 100 that includes a collection component 105 and a regulation component 110. The system 100 can be used to regulate medical treatment for an organism, such as a person. In one example, the system 100 is used to control an amount of medicine administered to the person. A medical control instruction 115 can be sent to the collection component 105. The collection component 105 can be configured to receive a medical control instruction 115. In one embodiment, a doctor enters a medical control instruction into a computer. The computer wirelessly sends the medical control instruction 115 to the system 100. Receiving the medical control instruction 115 can include obtaining the medical control instruction 115, reading the medical control instruction 115, storing the medical control instruction 115, making the medical control instruction 115 available to the regulation component 110, and others.

In one embodiment, the medical control instruction 115 is based, at least in part, on an organism medical information set for the organism. In one example, a medical professional determines a white blood cell count for a person. The white blood cell count can be part of the organism medical information set. The organism medical information set can include information specific to the person (e.g., a white blood cell count of the user), real-time information for the person (e.g., a current personal temperature), historical information of the person (e.g., how a user has previously responded to a medicine, how the current personal temperature compares with historical personal temperatures, and others), classification information of the person (e.g., a person's race, age, gender, blood type, line of work, activity level, smoking history, and others), family information of the person (e.g., how ancestors of the person have responded to a particular medicine), and others. While these examples are provided to frame some aspects of the breadth of such parameters, the above is in no way exhaustive or exclusive with respect to aspects herein.

The regulation component 110 can be configured to control (e.g., proactively control) an administration of a treatment 120 to the organism based, at least in part, on the medical control instruction 115. The treatment 120 can include a medicine dispensed, a medicine neutralized (e.g., convert the medicine into an inert compound, such as water), a procedure performed (e.g., cutting away a cyst), an improvement procedure (e.g., supply vitamins), and others. With the treatment 120, the administration can include increasing an amount of a medicine released, starting medicine release, stopping medicine release, lowering an amount of the medicine released, and others.

Figure 2:
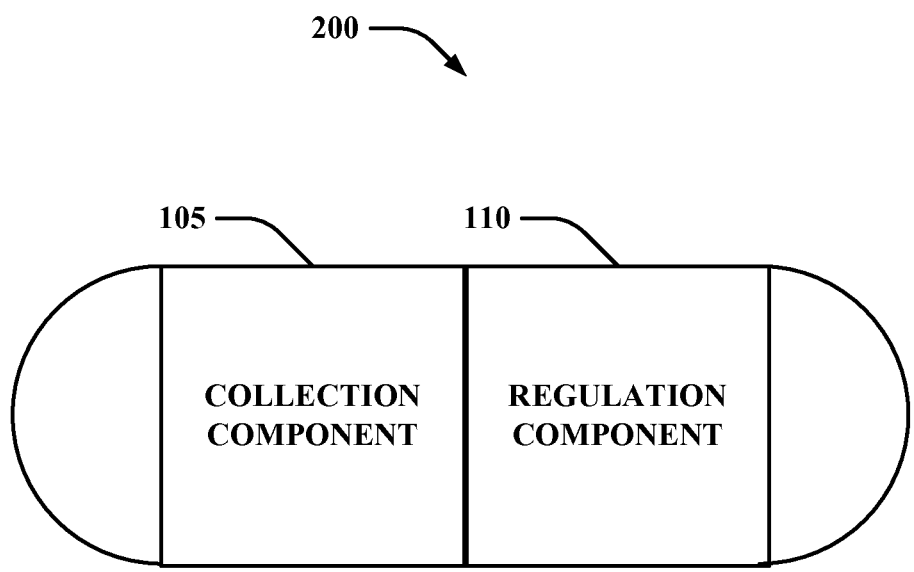

FIG. 2 illustrates one embodiment of a system 200 that includes the collection component 105 and the regulation component 110. In one embodiment, the collection component 105 and regulation component 110 are part of a pill. The pill can include a housing. The collection component 105 can be retained by the housing and/or the regulation component 110 can be retained by the housing. In one embodiment, the housing (e.g., a non-toxic plastic, a dissolvable non-toxic substance, and others) is orally ingestible by the organism (e.g., the person can ingest the pill). In one example, the pill is swallowed by the person without the pill having a physical connection outside the person.

In one embodiment, the system 200 can be inside the person. The system 200 can enter the user through injection, as a suppository, implantation, ingestion, and others. In one embodiment, the system 200 can be partially in the person and partially outside the person. For example, the system 200 can be part of a stint that exposes outside the skin and also resides within a blood vessel. In one embodiment, the system 200 can reside on the person (e.g., treatment is administered by placing medicine on a skin that is absorbed, an outward message provided to a designated area, and others). In one embodiment, the system 200 resides in a computer. The medical control instruction 115 of FIG. 1 is read by the collection component 105 and the regulation component 110 controls administration of the treatment 120 of FIG. 1 by wirelessly sending commands to a component capable of administering the treatment 120 of FIG. 1.

In one embodiment, the collection component 105 receives the medical control instruction 115 of FIG. 1 from a source outside the organism while the housing is ingested by the organism. In one example, the source is a computer that monitors a person (e.g., takes readings with an Electrocardiography machine, takes body temperature, and others). Based on a monitoring result, the medical control instruction 115 of FIG. 1 can be produced and sent (e.g., sent wirelessly) to the collection component 105 while the collection component 105 is within the person. The medical control instruction 115 of FIG. 1 can be followed by the regulation component 110 while the regulation component 110 is ingested by the person.

Figure 3:
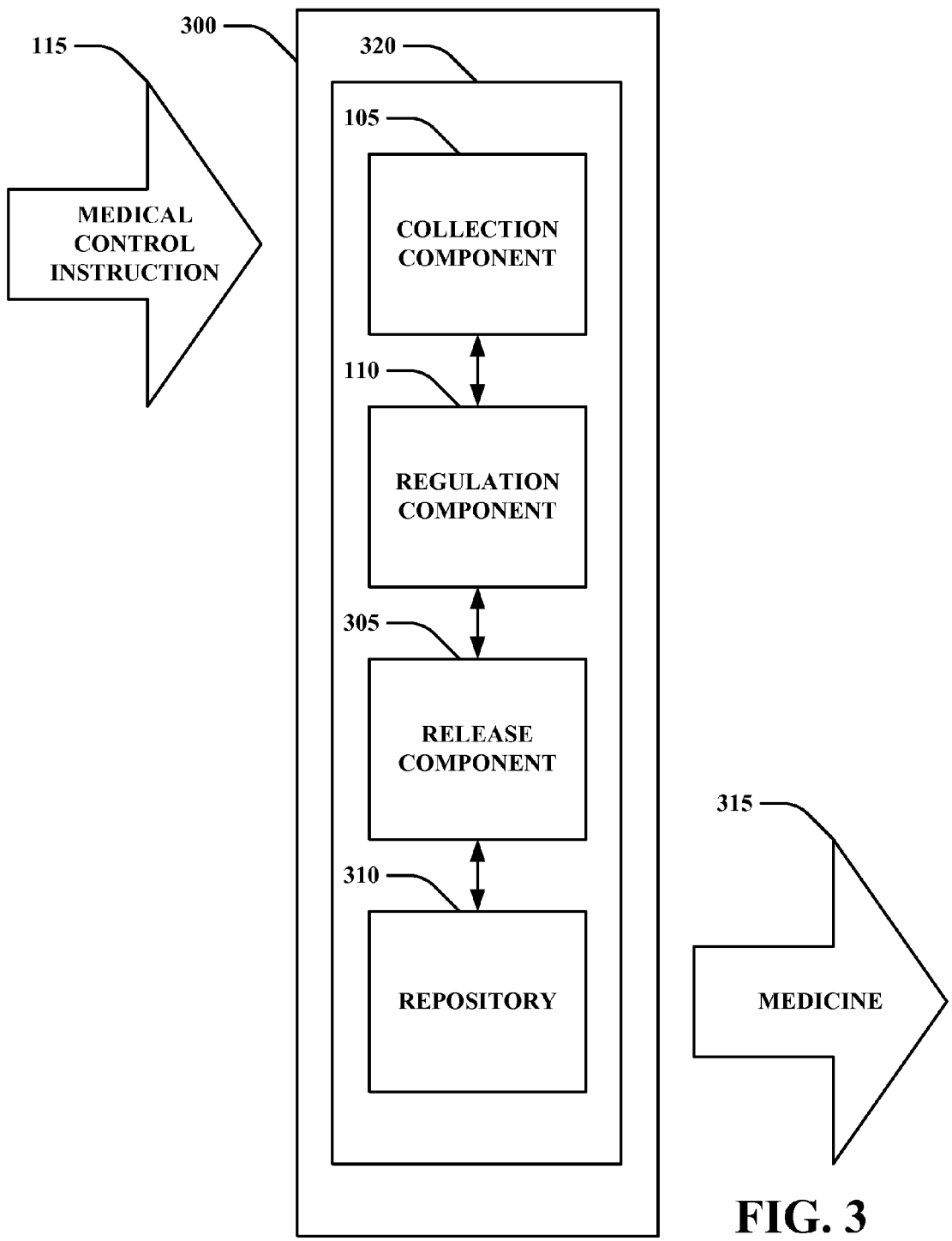

FIG. 3 illustrates one embodiment of a system 300 that includes a release component 305 and a repository 310. The collection component 105 can retain the medical control instruction 115 and the regulation component 110 can control administration of a treatment. In one example, the treatment comprises dispensing the amount of a medicine (e.g., the amount is the medicine 315). The regulation component 110 can communicate with the release component 305.

The release component 305 can be configured to dispense an amount of the medicine 315. In one example, the collection component 105 reads the medical control instruction 115 to instruct that B % of a medicine pool should be dispensed. The regulation component 110 controls the release component 305 to dispense B % of the medicine pool as medicine 315. The medicine pool can be retained in a repository 310. The medicine 315 can be dispensed from the repository 310. In one embodiment, a housing 320 can retain the repository 310, the release component 305, the collection component 105, the regulation component 110, at least one other component disclosed herein, or a combination thereof.

In one embodiment, the system 300 can include at least one staging area (e.g., within the housing 320). In one example, the repository 310 can include ten units of medicine. As is suggested, other embodiments can include virtually unlimited combinations of staging areas, units of medicine, and various other components (e.g. multiple staging areas for multiple substances and so forth). The medical control instruction 115 can indicate that three units of medicine be dispensed into the person. The release component 305 can open a door between the repository 320 and the staging area. While the door is open, medicine can transfer from the repository 320 and the staging area. In one embodiment, a fan system can be used to move medicine from the repository 320 and the staging area. The regulation component 110 can determine when Q units are in the staging area and send an instruction for the door to close. The regulation component 110 can determine when three units are in the staging area through monitoring transfer, weighing the staging area and/or repository, and others. When the door closes, a panel can open in the staging area that releases the medicine into the person. The door and panel can operate on a screw system where rotating a screw causes the door and panel to open or close. In one embodiment, the system 300 can employ a feedback loop that checks, for example, if the staging area is filled. While some specific aspects of mechanical or other means of accomplishing the storage, staging, and disbursement of a substance in accordance with features herein have been described above, one of ordinary skill in the art will readily appreciate that such descriptions are merely provided for example, and a variety of other solutions can be understood to accomplish these same ends (e.g., the system is by no means limited to, for example, doors, fans and screws).

Figure 4:
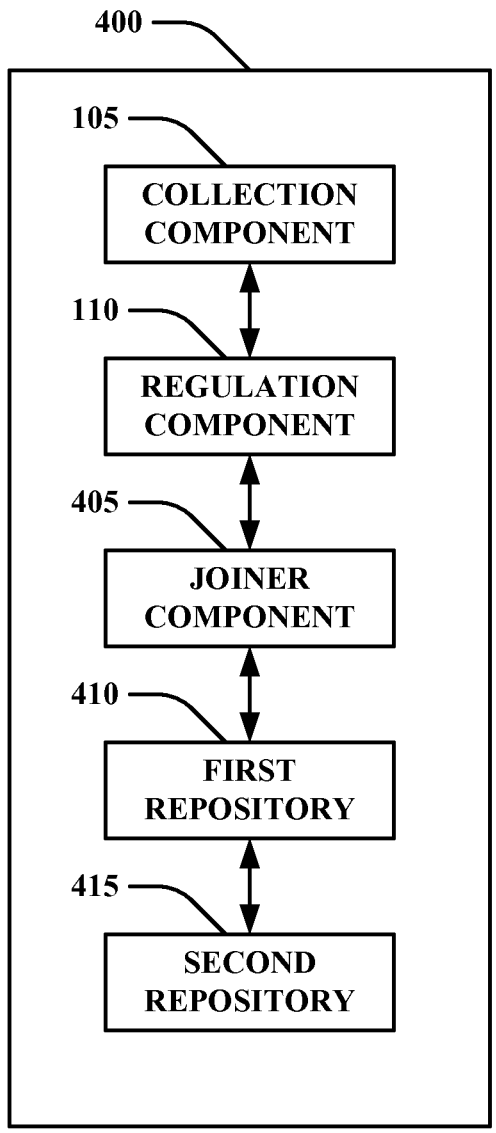

FIG. 4 illustrates one embodiment of a system 400 that includes a joiner component 405, a first repository 410, and a second repository 415. In one embodiment, a pill (e.g., a pill that includes the system 200 of FIG. 2) can be dissolved within a person. However, the pill can retain a repository that retains a relatively large amount of medicine. A fraction of the relatively large amount of medicine can be used and then the person can be cured, the person can achieve a desired metric (e.g., experience blood platelets within a specified range), and others. In an embodiment, the person can indicate if the desired metric has been achieved (e.g., pain relief). Despite this positive outcome, after the desired result is accomplished, a remaining medicine portion can be potentially harmful if released into the person when the person is well. Therefore, the joiner component 405 can be used in facilitating pill dissolving.

The joiner component 405 can be configured to combine the medicine with a substance. In one embodiment, combination of the medicine with the substance creates an inert compound. The inert compound can be a compound that can be safely released into the person. In one embodiment, the inert compound is water. In one example, combination of the medicine with the substrate chemically alters the medicine and the substrate.

In one embodiment, the medicine is housed in the first repository 410 and the substance is housed in the second repository 415. A housing can retain the first repository 410, the second repository 415, the joiner component 405, the collection component 105, and/or regulation component 110.

In one embodiment, the joiner component 405 can combine the medicine with the substance. The housing and components retained by the housing can be dissolved within the organism after the medicine is combined with the substance. In one embodiment, after combination, the substance is released into the person and then the housing is removed, dissuaded, dissolved, and others.

Figure 5:
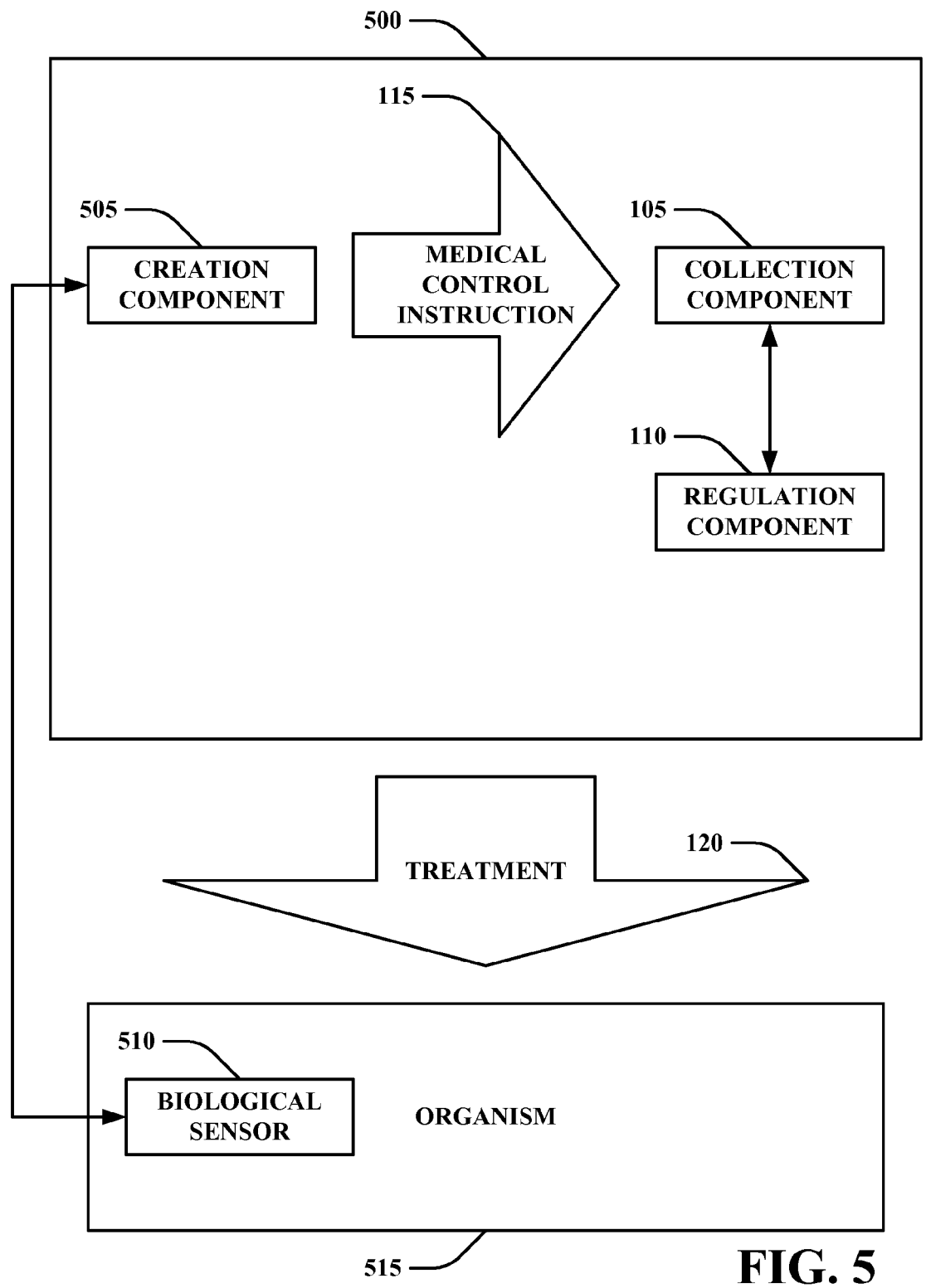

FIG. 5 illustrates one embodiment of a system 500 that includes a creation component 505. The creation component 505 can be configured to generate (e.g., select and produce, choose, create, and others) the medical control instruction 115 based, at least in part, on a sensor data set. In one embodiment, the sensor data set is real-time sensor data. The sensor data set can be produced by a biological sensor 510. In one embodiment, the sensor data set is data obtained by the biological sensor 510 pertaining to an organism 515. In one embodiment, the biological sensor 510 can be part of the system 500.

In one embodiment, the creation component 505 can be configured to generate the medical control instruction 115 based, at least in part, on the sensor data set and on a historical characteristic of the organism 515. Example historical characteristics can be historical reactions to medicines, historical medical data (e.g., body temperature, blood pressure, and others), previous medical procedures undergone, and others.

In one embodiment, the creation component 505 can be configured to generate the medical control instruction 115 based, at least in part, on the sensor data set and on a classification characteristic of the organism 515. In one example, a person can fit into different classifications where different classifications include different characteristics. In one example, a classification is that a person is a male or female. Males can typically have a first response to the medicine while females typically have a second response to the medicine. If the person is a female, then the creation component 505 can consider the second response when generating the medical control instruction 115. Example classifications can include race, gender, height, weight, family history, and others. This list is not intended to be exhaustive, but rather provide a concise insight into the aspects that can be considered when approaching the issue of classifications.

Figure 6:
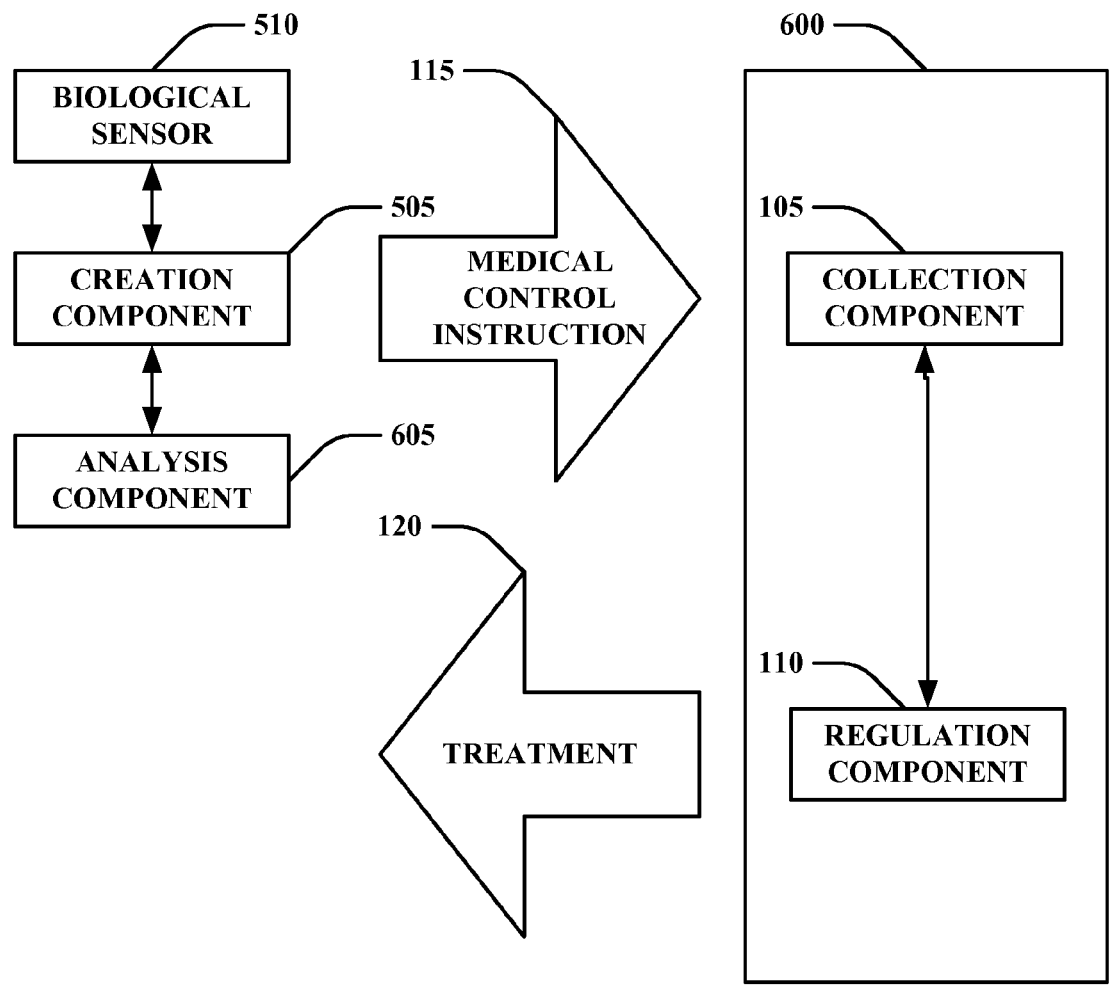

FIG. 6 illustrates one embodiment of a system 600 that includes the collection component 105 and the regulation component 110. The creation component 505, the biological sensor 510, and/or an analysis component 605 can function outside of the system 600 and/or be part of the system 600. In one embodiment, the biological sensor 510 measures a physiological response (e.g., physiological response to a treatment, physiological response to a stimulation, and others) which can comprise a chemical response, an electrical response, a muscular response, a temperature response, a combination thereof, or others.

Medical information and other information can be collected for a person by the biological sensor. In one example, at least one biological sensor 510 can be employed to determine various characteristics of a patient (e.g., when the patient is the organism 510 of FIG. 5). The biological sensor 510 can determine, for example, heart rate, blood pressure, white blood cell count, fever, glucose level, and other measurements for or relating to the patient. The preceding aspects are not exhaustive or exclusive, and merely demonstrate succinct points for some aspects of biological sensor 510 (or sensors) scope (or scopes). Information determined by the biological sensor 510 can be analyzed by the analysis component 605 to produce an analysis result. The analysis result can be used by the creation component 505 to select and generate the medical control instruction 115.

In one example, the creation component 505 can retain an internal chart relating fever level to medicine dispensed. A fever level can be ascertained by the biological sensor 510 and the analysis component 605 can determine an appropriate treatment by comparing the fever level with the chart (e.g., find the fever level on the chart and then find a corresponding treatment). The creation component 505 can generate the medical control instruction 115, where the medical control instruction 115 instructs an entity to employ the appropriate treatment. The medical control instruction 115 can be sent to the collection component 105 that receives the medical control instruction 115. The regulation component 110 can control an administration of the treatment 120 (e.g., the appropriate treatment) based, at least in part, on the medical control instruction 115.

Figure 7:
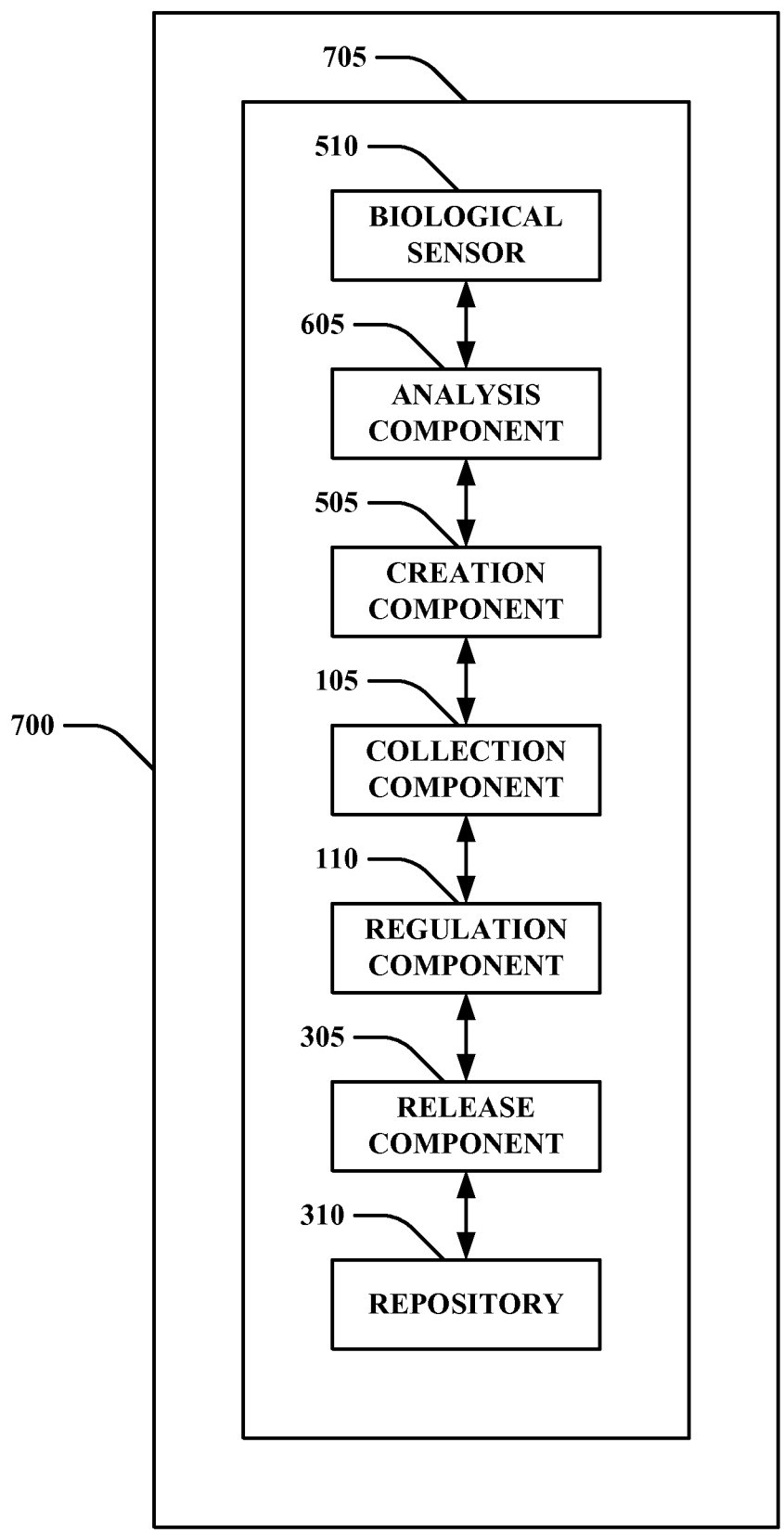

FIG. 7 illustrates one embodiment of a system 700 that includes an ingestible housing 705. The ingestible housing 705 can retain the biological sensor 510, the creation component 505, the collection component 105, and the regulation component 110. Additionally, the ingestible housing 705 can retain the analysis component 605, release component 305, and other components and entities (e.g., the repository 305) disclosed herein. In one embodiment, the collection component 105, regulation component 110, biological sensor 510, and creation component 505 can be configured to function while the ingestible housing 705 is within an organism.

In one embodiment, the regulation component 110 administers a treatment to an organism. The biological sensor 510 can make a determination of at least part of a reaction the organism has to the treatment. The determination can produce a medicine reaction data set based, at least in part, on the reaction. The medicine reaction data set can be at least part of the sensor data set.

In one embodiment, the creation component 505 is configured to generate a subsequent medical control instruction. The subsequent medical control instruction can be based, at least in part, on the medicine reaction data set. The regulation component 110 can control administration of a subsequent treatment based, at least in part, on the subsequent medical control instruction.

In one example, a person can be subjected to a medicine that drastically improves the person's physical state (e.g., radically reduces a fever). The biological sensor 510 can detect this improvement and notify the creation component 505. The creation component 505 can determine that more of the medicine should be provided to the person and subsequently create a medical control instruction to increase a medicine amount.

Conversely, in one example, the person can be subjected to a first medicine that drastically makes the person's physical state worse (e.g., significantly increases a fever). The biological sensor 510 can detect this negative reaction and notify the creation component 505. The creation component 505 can determine that no more of the first medicine should be provided to the person, a second medicine should be provided, and a counter-agent to the first medicine should be provided to the person (e.g., the creation component 505 selects the second medicine and counter-agent). The creation component 505 can create a medical control instruction for implementing a supplemental treatment and the regulation component 110 can control administration of the supplemental treatment. Additionally, a user profile can be proactively updated with allergy information, the medicine reaction data set, the sensor data set, and others (e.g., the collection component can transmit information).

Figure 8:
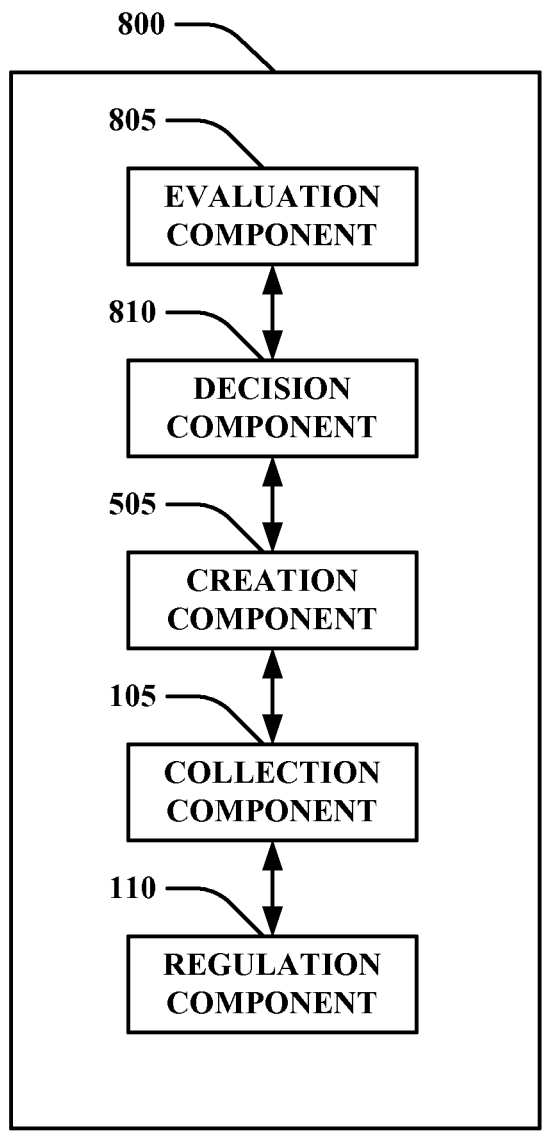

FIG. 8 illustrates one embodiment of a system 800 that includes an evaluation component 805 and a decision component 810. The evaluation component 805 can be configured to analyze the sensor data set produced by the biological sensor 510 of FIG. 5 to produce a sensor data set analysis result. The decision component 805 can be configured to determine if the creation component 505 generates the medical control instruction. This determination can be based, at least in part, on the sensor data set analysis result. In one embodiment, the creation component 505 generates the medical control instruction in response to a positive determination (e.g., a determination that the medical control instruction should be generated). In response to the positive determination, the creation component 505 can generate the medical control instruction and send the medical control instruction to the collection component 105. The collection component 105 can read the medical control instruction and notify the regulation component 110 on how to administer a treatment.

In one embodiment, a permanent or semi-permanent medicating structure may be associated with a person. In one example, a medicating structure may be integrated into a chest port. The medicating structure can include the system 800. The system 800 can include the biological sensor 510 of FIG. 5 and/or the biological sensor 510 of FIG. 5 can function outside of the system 800. The medicating structure can be in a continuous state of readiness to dispense a medicine. In one example, if a person experiences lung inflammation, an anti-inflammatory can be administered to the person. The system 800 can continuously monitor the person and determine if the person should be treated with medicine. In one example, breathing rate can be analyzed against a baseline for the person and/or people in the person's classification to determine if medicine should be administered. If a determination is made that medicine should be administered, then the system 800 can function to cause administration of the medicine to occur.

Figure 9:
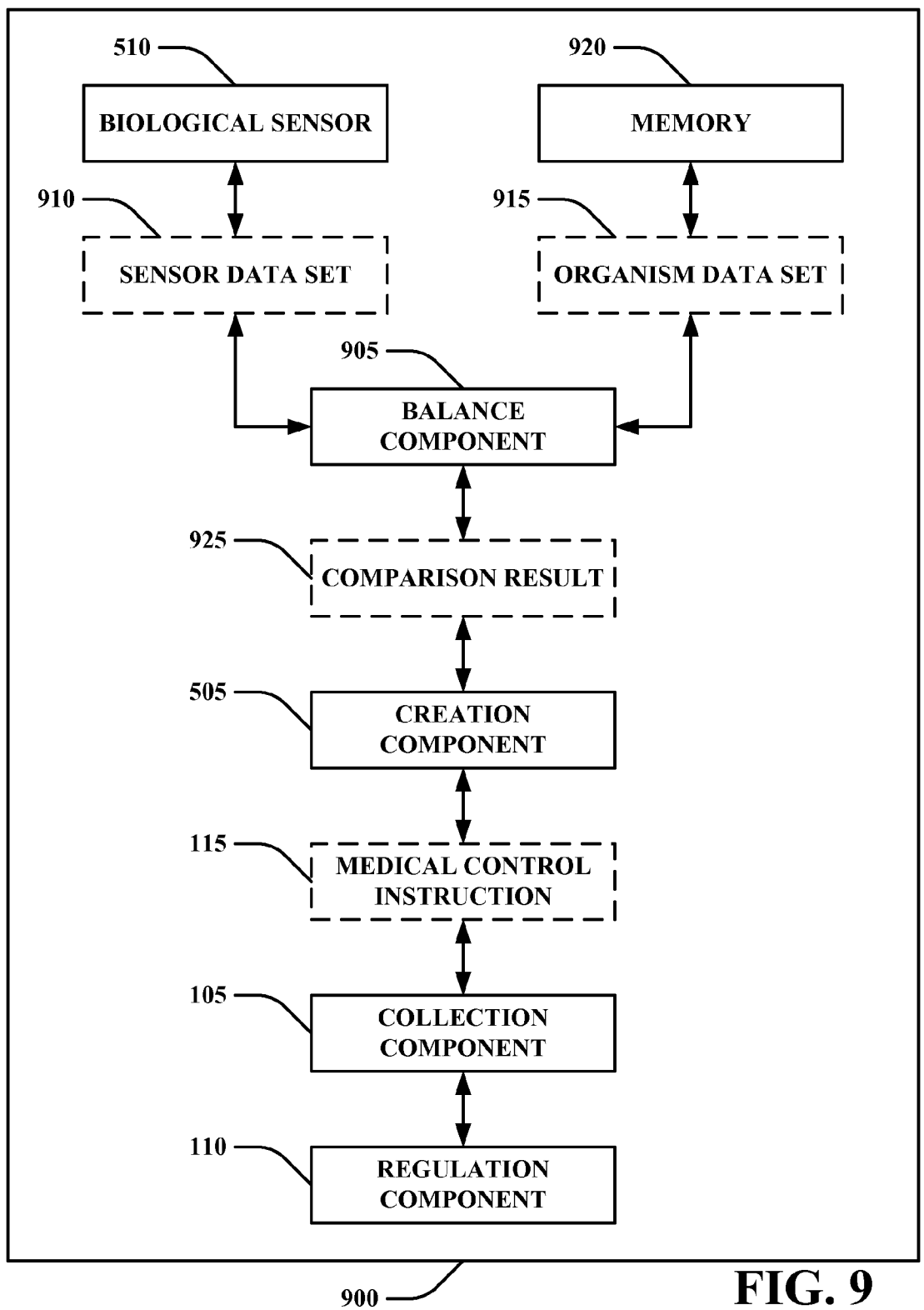

FIG. 9 illustrates one embodiment of a system 900 that includes a balance component 905. The system 900 can include the biological sensor 510 that can be used to produce a sensor data set 910. In addition to the sensor data set 910, an organism data set 915 can be produced. In one example, a memory 920 can retain the organism data set 915. The organism data set 915 can include historical organism information, organism classification information (e.g., a person's classification, medical information about a classification, and others), organism metadata, and others.

The balance component 905 can be configured to compare the sensor data set 910 against the organism data set 915 to produce a comparison result 925. The comparison result 925 can be used by the creation component 505 to generate the medical control instruction 115 and/or by the decision component 810 of FIG. 8 to determine if the medical control instruction 115 should be generated. The medical control instruction 115 can be used by the collection component 105 and the regulation component 110.

In one example, an average person can have an internal body temperature of 98.6° F. However, a specific person may have an average internal body temperature of 98.9° F. The biological sensor 510 can determine that the specific person has an internal body temperature of 98.9° F. While this internal body temperature may normally indicate a fever, for the specific person the temperature is actually normal. The balance component 905 can compare the internal body temperature of the specific person against the average internal body temperature of the specific person and determine that a fever does not exist. Therefore, the balance component 905 can determine that the medical control instruction 115 should not be generated.

In one example, the sensor data set 910 can indicate that a person has an internal body temperature of 98.9° F. While the internal body temperature may indicate a fever, the organism data set 915 can show that historically the person has been able to reduce temperatures of 99.0° F. and below naturally and without medication. Therefore, the balance component 905 can determine that the medical control instruction 115 should not be generated.

In one example, the sensor data set 910 can indicate that a person has an internal body temperature of 98.6° F. While the internal body temperature may indicate no medical problems, the organism data set 915 can show that for the person this is a fever temperature. Therefore, the balance component 905 can determine that the medical control instruction 115 should be generated in order to reduce or eliminate the fever.

In one embodiment, the sensor data set 910 can be used to update, augment, and perform other tasks upon the organism data set 915. The balance component 905 can function such that the sensor data set 910 is so extreme that the organism data set 915 is ignored. In one example, if a person has internal body temperature of 101.5° F. or above, treatment can automatically occur (e.g., a medical control instruction is generated and followed) without consideration to the organism data set 915.

Figure 10:
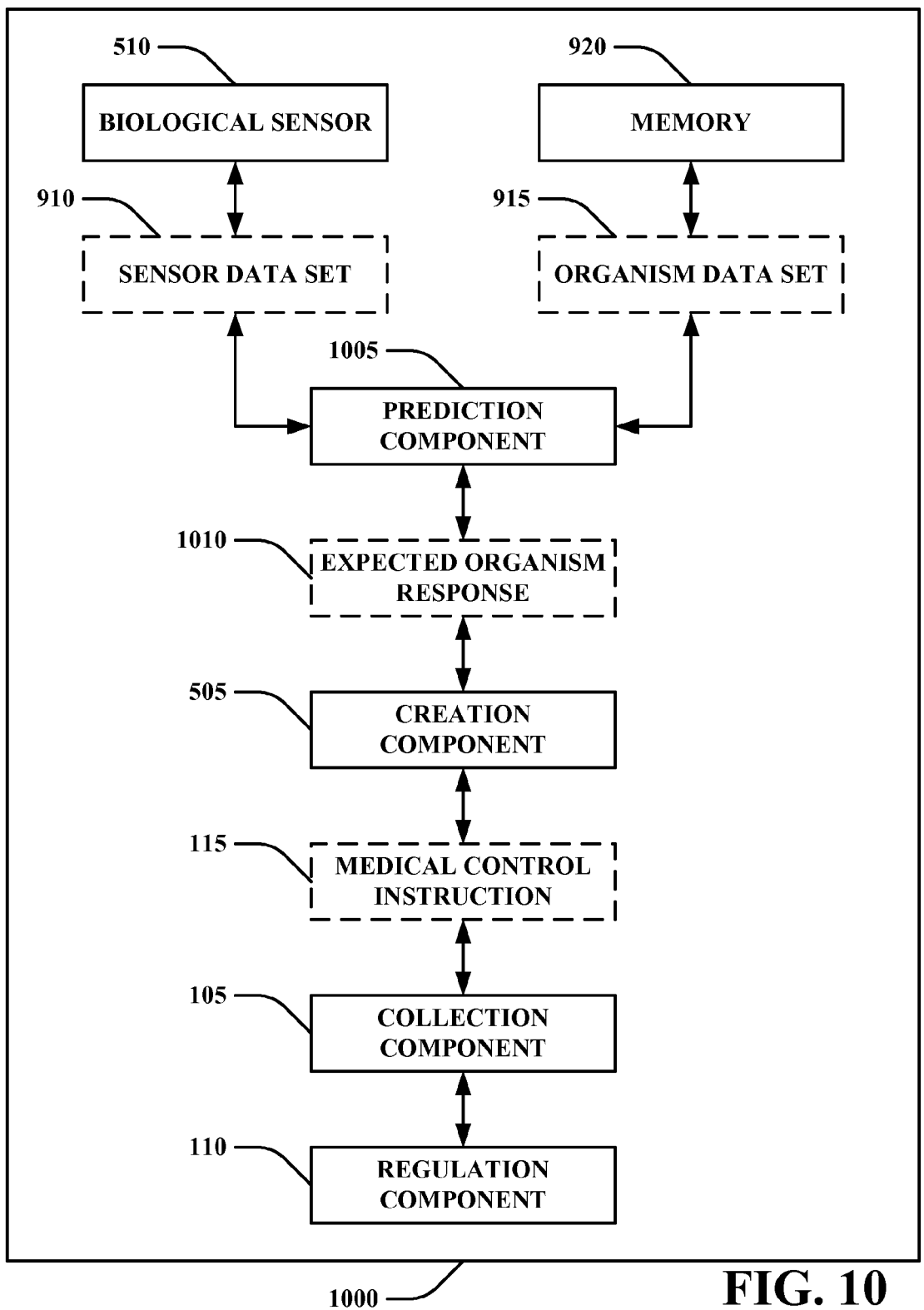

FIG. 10 illustrates one embodiment of a system 1000 that includes a prediction component 1005. The system 1000 can include the biological sensor 510 that can be used to produce the sensor data set 910. The biological sensor 510 can be multiple specific sensors (e.g., a temperature sensor, a blood pressure sensor, and others), an all-purpose sensor, and others. The biological sensor 510 can be an internal sensor, an external sensor, a measurement device (e.g., mercury thermometer), a computer, an input table for a user to enter symptoms, and others. In addition to the sensor data set 910, an organism data set 915 can be produced. In one example, a memory 920 can retain the organism data set 915. The organism data set 915 can include previous responses to a certain treatment.

The prediction component 1005 can be configured to forecast an expected organism response 1010 to the treatment. The expected organism response 1010 can be based, at least in part, on the sensor data set 910 and/or the organism data set 915. In one embodiment, the creation component 505 can be configured to generate the medical control instruction 115 based, at least in part, on the expected organism response 1010. The collection component 105 can receive the medical control instruction 115 and the regulation component 110 can cause a treatment to occur according to the medical control instruction 115.

Based on the sensor data set 910 and the organism data set 915, the prediction component 1005 can forecast how a person is expected to respond to a treatment. In one example, a person can have a fever. Two medicines can be available to treat the fever: Medicine A and Medicine B. Medicine A can have a better result with relatively high fevers while Medicine B can have a better result with relatively low fevers (e.g., this information can be obtained from the memory 920). The sensor data set 910 can indicate that the person has a relatively high fever. However, the organism data set 915 can include a personal history that indicates that the person did respond as expected previously to a medicine with similar characteristics to Medicine A and no information is available for Medicine B or a medicine similar to Medicine B. Thus, there can be contradictory information for Medicine A and limited information for Medicine B. The prediction component 1005 can balance the contradictory information and limited information to determine if Medicine A or Medicine B should be used as a treatment for the person. Based on a determination made, the prediction component 1005 can instruct the creation component 505 to generate a medical control instruction. Returning to the previous example, the prediction component can balance the sensor data set 910 against the organism data set 915 to determine that Medicine B should be used as a treatment. A notice can be transferred to the creation component 505 to generate a medical control instruction 115 for Medicine B.

In one embodiment, various precautions can occur to protect the organism from an incorrect treatment. Examples of an incorrect treatment can include over-medication, under-medication, performing a treatment, not performing a treatment, exceeding a medicine threshold, and others. In one example, the creation component can verify the determination of the prediction component 1005 before generating and/or sending the medical control instruction 115. In one example, the collection component 105 can analyze the medical control instruction 115 before making the medical control instruction 115 available to the regulation component 110. In one example, prior to administering the treatment, the regulation component 110 can communicate with the creation component 505 (e.g., communicate by way of the collection component 105) to determine if the medical control instruction 115 is free of corruption. If the medical control instruction 115 is corrupted, then a subsequent instruction can be generated and sent by the creation component 505. In one embodiment, a treatment is not administered until a medical professional authorizes the treatment. In one embodiment, the medical control instruction 115 is communicated in an encrypted manner.

Figure 11:
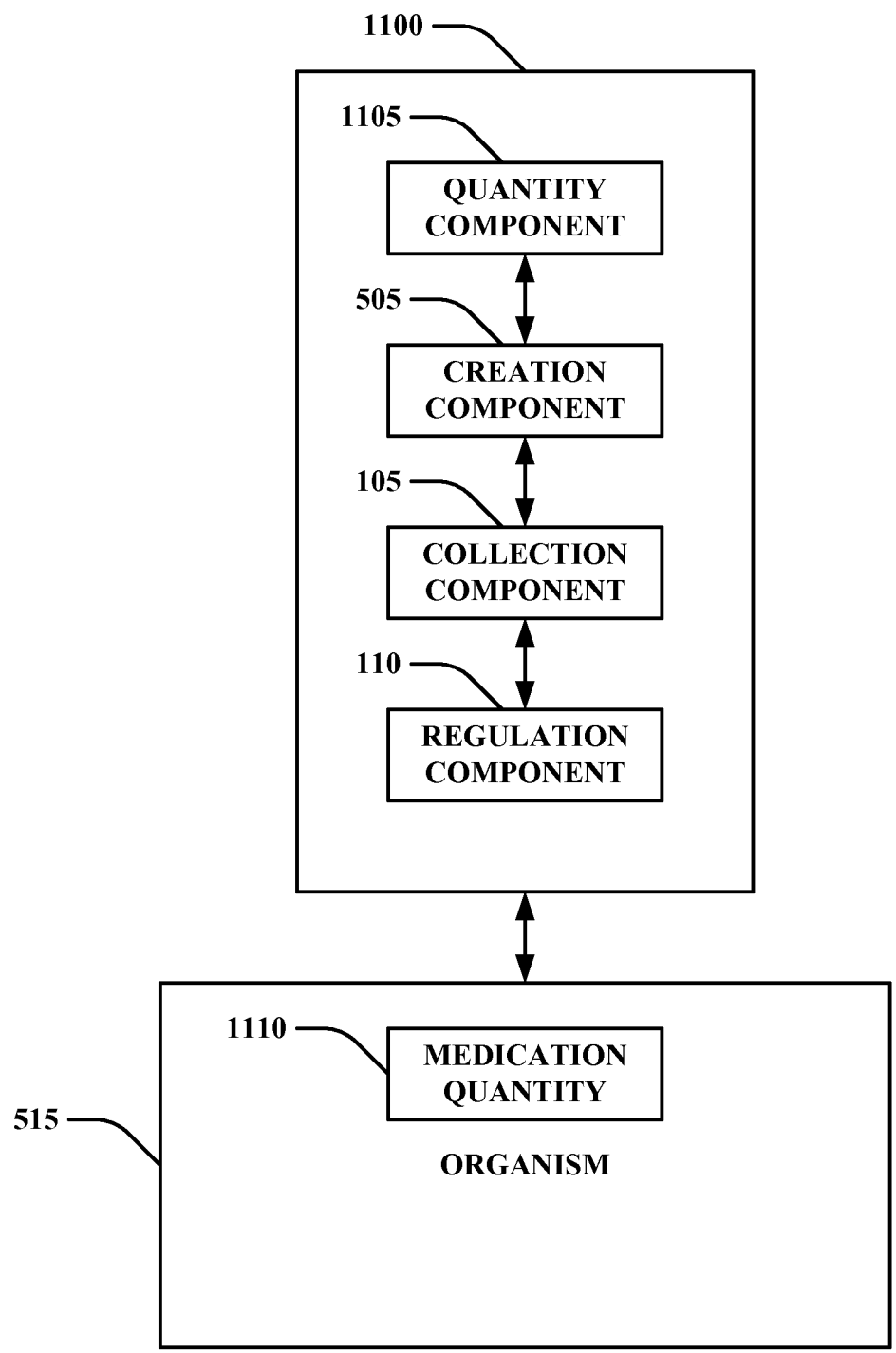

FIG. 11 illustrates one embodiment of a system 1100 that includes a quantity component 1105. The quantity component 1105 can be configured to identify a medication quantity 1110 in the organism 515. The creation component 505 can be configured to generate the medical control instruction 115 of FIG. 1 based, at least in part, on the sensor data set 910 of FIG. 9 and on the medication quantity 1110. The medical control instruction 115 of FIG. 1 can be used by the collection component 105 and regulation component 110.

In one embodiment, a treatment for a person can be dispensing medicine to the person. The medicine can be dispensed in different quantities. In one example, the medicine is dispensed as desired (e.g., the person indicates when more medicine should be released), based on a reading being met (e.g., the person having a fever above 98.6° F.), periodically, and others. However, an amount of medicine within the person can influence how much medicine is given and/or if medicine is given at all. Therefore, the quantity component 1105 can identify the medication quantity 1110 and make the medication quantity 1110 known to the creation component 505.

In one embodiment, information for the medication quantity 1110 is used to determine if a treatment was previously administered. In one example, if the medication quaintly 1110 is greater than zero, than a positive determination can made that the treatment was administered. However, if the medication quaintly 1110 is equal to zero, than a positive determination can be made that the treatment was not administered and/or previous treatment administration is not determinable from the medication quantity 1110. In one embodiment, the creation component 505 generates the medical control instruction 115 of FIG. 1 in response to the medication quantity 1110 reaching zero.

Figure 12:
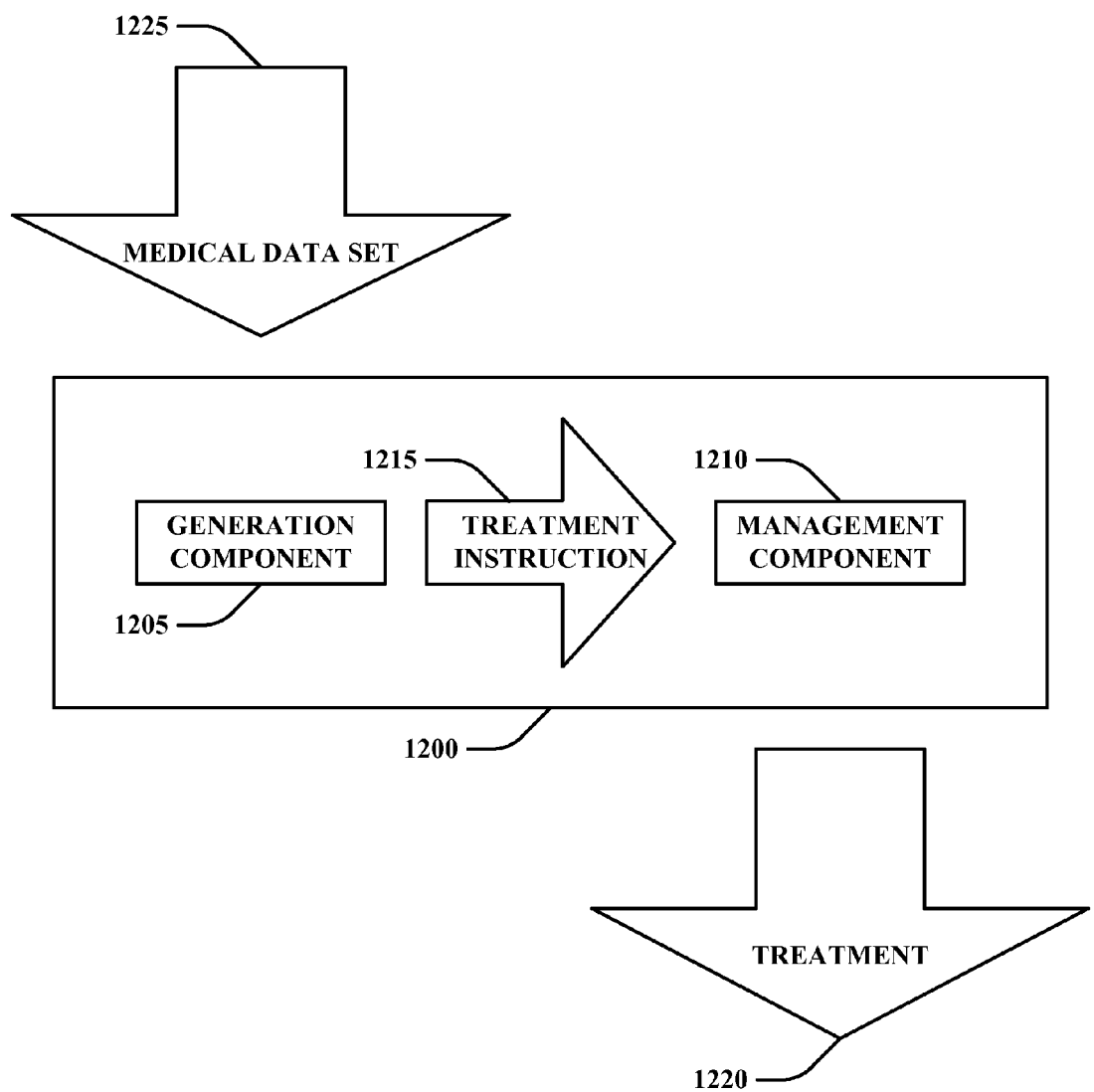

FIG. 12 illustrates one embodiment of a system 1200 that includes a generation component 1205 and a management component 1210. The generation component 1205 can be configured to produce a treatment instruction 1215 for controlling administration of a treatment 1220 to an organism. In one embodiment, the treatment instruction 1215 is based, at least in part, on a medical data set 1225. The medical data set 1225 can comprises real-time health information for the organism. Examples of real-time health information can include temperature measurements, medicine in the organism, bone structure, muscle structure, and others.

The management component 1210 can be configured to control the treatment to be administered based, at least in part, on the treatment instruction. In one embodiment, the regulation component 110 of FIG. 1 is part of the management component 1210. In one embodiment, the management component 1210 is part of the regulation component 110 of FIG. 1. In one embodiment, the creation component 505 of FIG. 5 is part of the generation component 1205. In one embodiment, the generation component 1205 is part of the creation component 505 of FIG. 5.

In one embodiment, a housing retains the generation component 1205 and management component 1210. The housing can be configured to be within the organism (e.g., while the generation component 1205 and/or management component functions).

In one embodiment, a memory (e.g., the memory 920 of FIG. 9) retains at least one piece of information associated with the generation component 1205 or the management component 1210. In one example, the memory retains at least part of the generation component 1205 or the management component 1210. In one example, the memory retains an instruction to control the generation component 1205 or the management component 1210.

The following methodologies are described with reference to figures depicting the methodologies as a series of blocks. These methodologies may be referred to as methods, processes, and others. While shown as a series of blocks, it is to be appreciated that the blocks can occur in different orders and/or concurrently with other blocks. Additionally, blocks may not be required to perform a methodology. For example, if an example methodology shows blocks 1, 2, 3, and 4, it may be possible for the methodology to function with blocks 1-2-4, 1-2, 3-1-4, 2, 1-2-3-4, and others. Blocks may be wholly omitted, re-ordered, repeated or appear in combinations not depicted. Individual blocks or groups of blocks may additionally be combined or separated into multiple components. Furthermore, additional and/or alternative methodologies can employ additional, not illustrated blocks, or supplemental blocks not pictured can be employed in some models or diagrams without deviating from the spirit of the features. In addition, at least a portion of the methodologies described herein may be practiced on a computer-readable medium storing computer-executable instructions that when executed by a computer cause the computer to perform a methodology.

Figure 13:
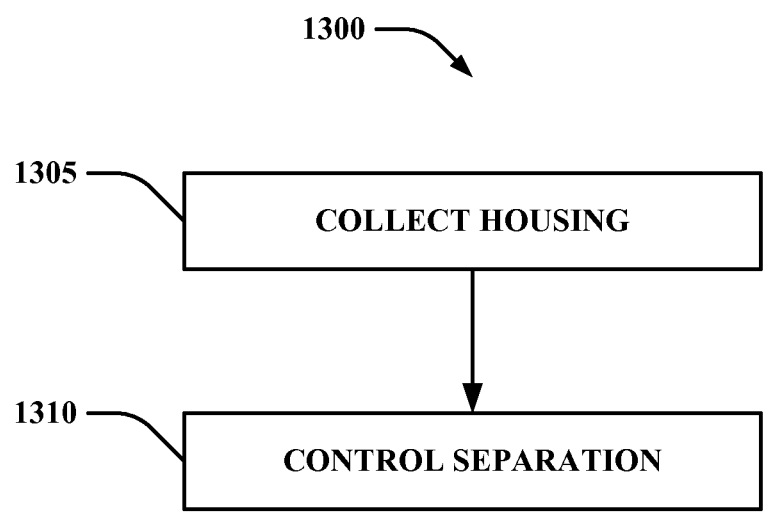

FIG. 13 illustrates one embodiment of a method 1300 for collecting a housing and controlling a separation. In one embodiment, a housing can have a replicable medicine repository. The housing can be a pill that passes through a person. The pill can enter the user (e.g., be orally taken), dispense medicine, and then exit the user (e.g., through the gastrointestinal tract). Once the pill exits the user, the repository can be re-filled and/or removed. The removed repository can be replaced with another repository. In one or more embodiments, contents or components of the pill or the repository can be recycled or reused.

The method, at 1305, can include collecting a housing (e.g., an orally ingestible housing) after the housing exits an organism (e.g., passes through a gastrointestinal tract of the organism). In one embodiment, the housing is configured to regulate medicine dispensing to the organism. The method, at 1310, can include controlling a separation of a medicine component of the housing from a non-medicine component of the housing. The medicine component and/or non-medicine component can be sterilized and then become part of separate housings, rejoin, be disregarded, and others. In one embodiment, the housing is formed from combination of the medicine component with the non-medicine component.

Figure 14:
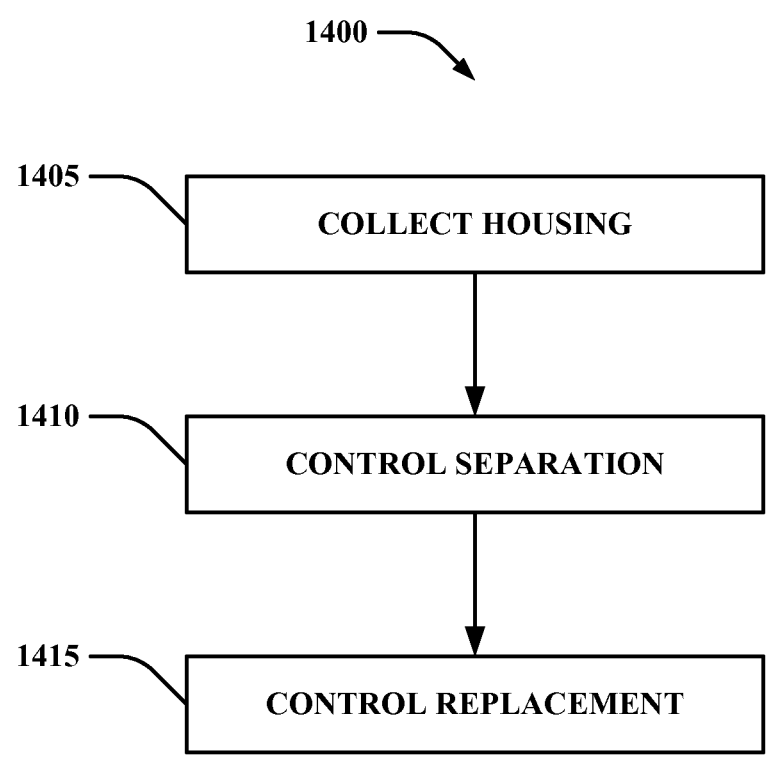

FIG. 14 illustrates one embodiment of a method 1400 for controlling a replacement of a medical component. At 1405, collecting a housing after the housing exits an organism can occur. In one embodiment, the housing is configured to regulate medicine dispensing to the organism. At 1410, the method 1400 can include controlling a separation of a medicine component of the housing from a non-medicine component of the housing. The method 1400, at 1415, can include controlling a replacement of the medicine component by a supplemental component in the housing after the medicine component is separated from the non-medicine component.

In one example, the housing is a structure that can be inserted into a person. The structure can be removed and placed into a machine (e.g., the machine collects the housing). The machine can remove the medical component and integrate a replacement medical component. In one embodiment, the medical component and replacement medical component include one medicine or different medicines. After removal of the medical component, the medical component can be refilled, disregarded, and/or have other processes or uses applied.

Figure 15:
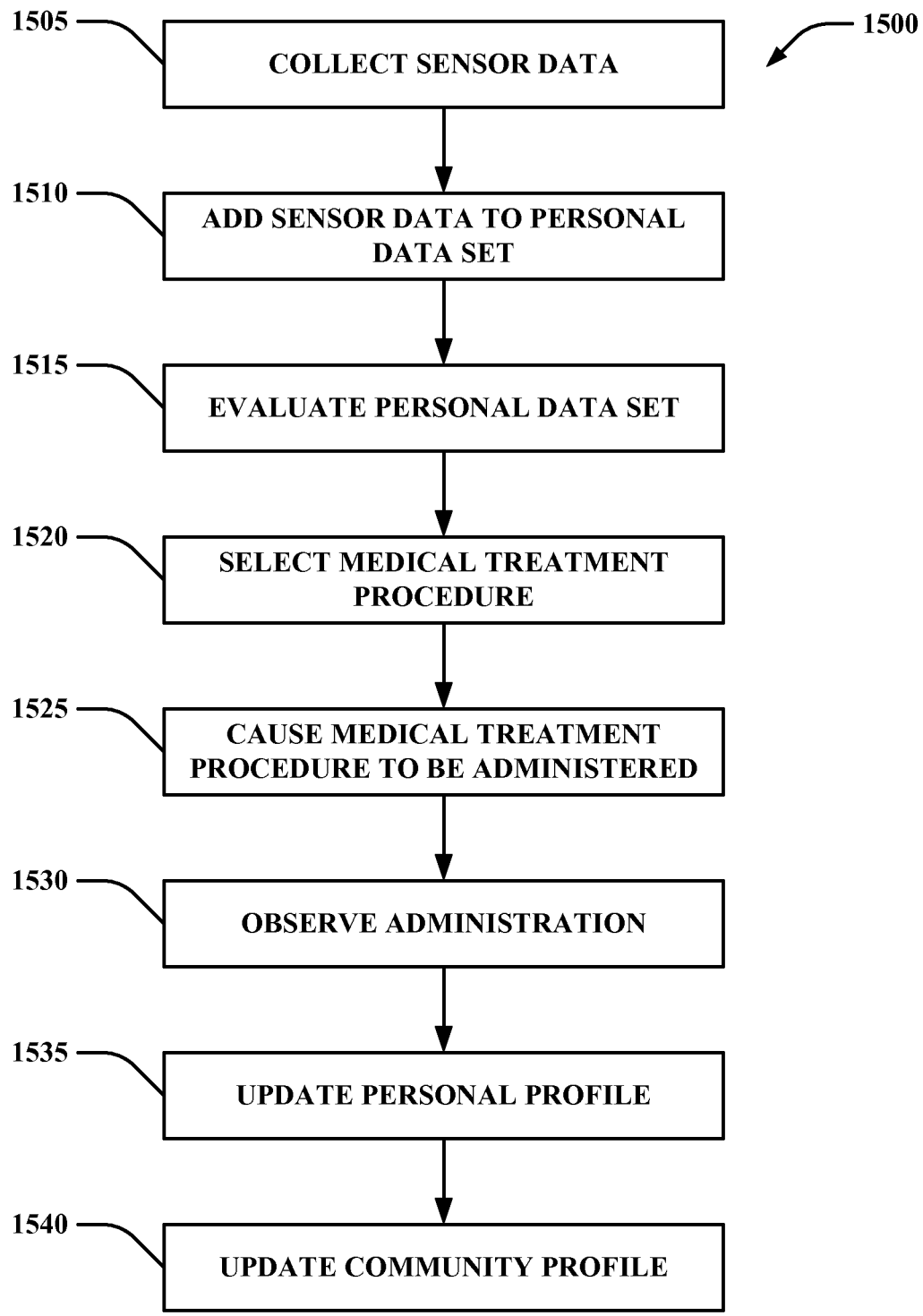

FIG. 15 illustrates one embodiment of a method 1500 for management of a personal profile. A person can have a personal profile that includes their personal identification information, classification information, medical information, information collected from a sensor, and others. Updates to the personal profile can occur as information is learned, information changes, medical procedures are enacted, and others.

The method 1500, at 1505, can include collecting sensor data and, at 1510, can include adding the sensor data to a personal data set. Various sensors can obtain information about the person. Example information is blood pressure, glucose level, and others. This information can be aggregated together into the personal data set. In addition, information ascertained from a sensor can be added to an existing personal data set.

At 1515, the method 1500 can include evaluating the personal data set. In one example, recently taken sensor information can be compared with personal baseline information to determine if the person is suffering from an illness. Based on a result of this evaluation, at 1520, a medical treatment procedure can be selected. In one embodiment, a determination is made on if the person is sick. If a determination is made that the person is sick, then the medical treatment procedure is selected.

The method 1500, at 1525, can include causing the medical treatment procedure to be administered. The administration can be observed at 1530 and based on this observation, at 1535, an update can be made to the personal profile. In one example, the person can have an allergic reaction to a medicine applied during a medical treatment procedure. The allergic reaction can be noted in the personal profile (e.g., so the medicine is not again given to the person). In one embodiment, the medical treatment procedure can include multiple medicines being given to the person. The person can have an allergic reaction to a medicine, but since multiple medicines are given it can be difficult to determine which medicine causes the allergic reaction. Information can be analyzed to determine which medicine causes the allergic reaction. In one embodiment, the personal profile can be evaluated to identify other medicines the person is allergic to and at least one artificial intelligence technique can be used to determine which medicine caused the allergic reaction.

Additionally, a community profile can be updated at 1540. The community profile can be a profile for a group of users. In one example, the community profile is a profile for a specific set of people (e.g., a set of people who opt-in to the community profile). In one example, the community profile is a profile for a classification of people (e.g., people who live in a certain city or geographical area, people of a certain age & race, and others). The community profile can be used to select a medical treatment, determine if a medical treatment is appropriate, and others.

Figure 16:
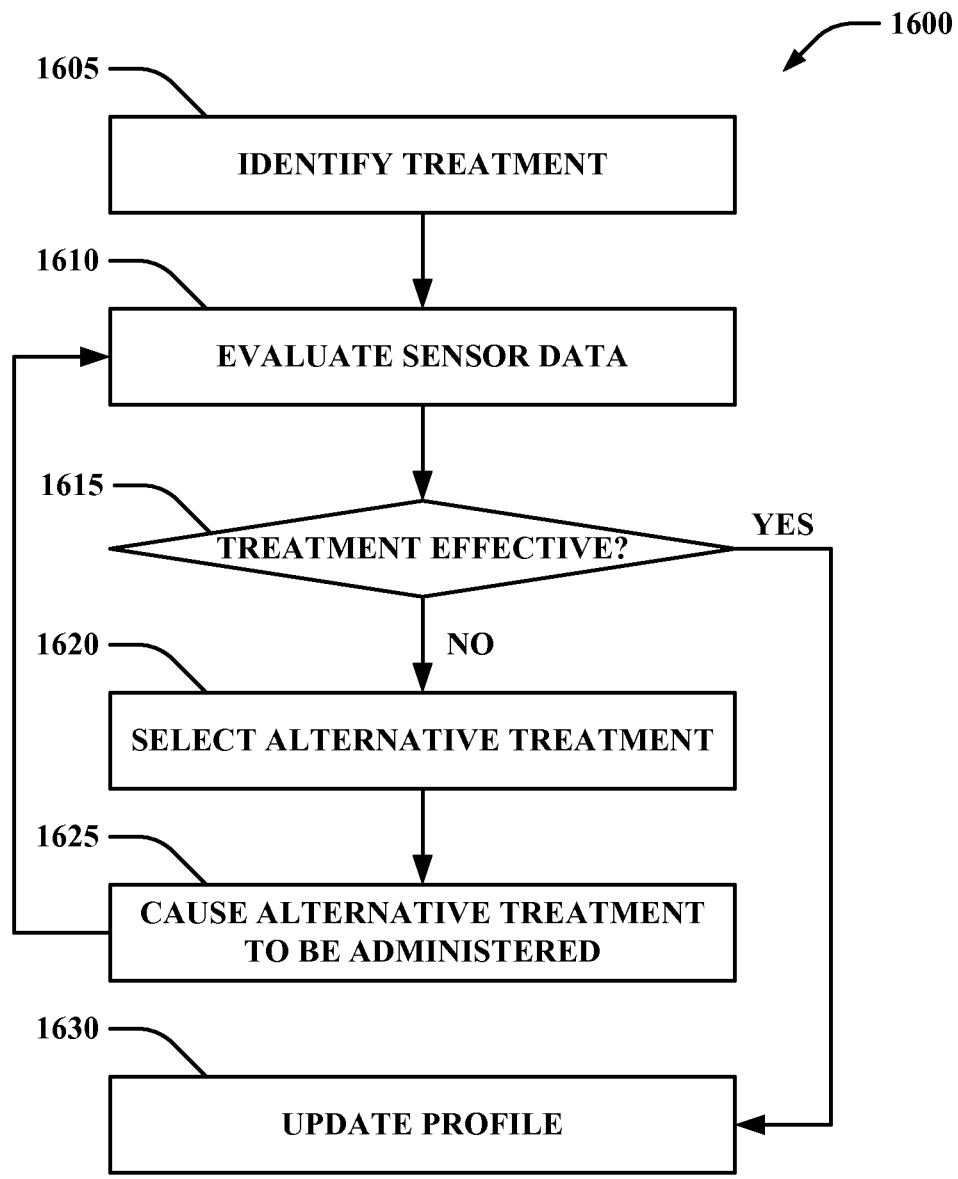

FIG. 16 illustrates one embodiment of a method 1600 for evaluating treatment effectiveness. An organism (e.g., a person) can be subjected to a medical treatment. While effort can be expended on selecting a proper treatment, it may be possible for a selected treatment to be relatively ineffective. Therefore, a subsequent medical treatment can be selected and administered.

At 1605, a treatment can be identified. In one example, the treatment is administered and a sensor identifies administration of the treatment. Additionally, at least one sensor can be used to determine how the person responds to the treatment. In one example, sensor data for a body temperature can be collected for before a treatment is administered and after a treatment is administered.

At 1610, sensor data can be evaluated. Based, at least in part, on sensor data evaluation a determination is made at 1615 on if a treatment is effective. In one example, treatment effectiveness can include if the body temperature is lowered after treatment is administered, if the body temperature is lowered sufficiently after treatment is administered, and others.

If the determination is made that the treatment is not effective, then the method 1600 can continue to 1620 where an alternative treatment is selected. In one embodiment, when an initial treatment is selected, multiple treatments are ranked and a highest ranking treatment is selected as the initial treatment. The alternative treatment can be a second-highest ranking treatment. In one embodiment, information on how the person responds to the initial treatment can be used in selecting the alternative treatment. In one example, if the person has no reaction to a treatment medicine, then medicines with similar characteristics to the treatment medicine can be ignored when selecting the alternative treatment. At 1625, the alternative treatment can be caused to be administered. If the determination made at 1615 is that the treatment is effective, then, at 1630, a personal profile can be updated indicating that the treatment is effective.

Figure 17:
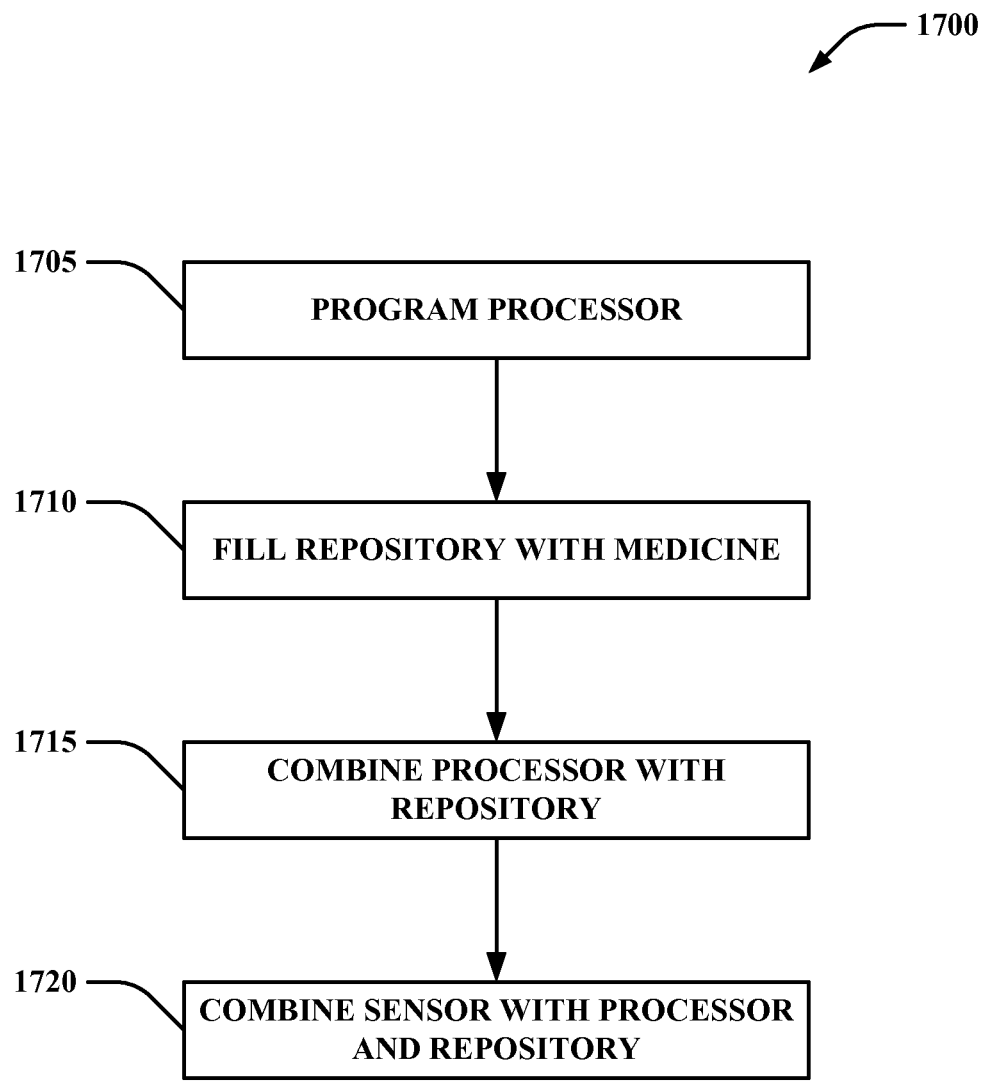

FIG. 17 illustrates one embodiment of a method 1700 for creating an apparatus for treatment. A processor can be programmed at 1705. Programming the processor can include adding instructions for when to dispense medicine, when to convert the medicine into an inert compound, and others. At 1710, a repository can be filled with medicine and, at 1715, the repository can be combined with the processor. At 1720, a sensor can be combined with the repository and processor. Other items can be combined with the repository, processor, and sensor, such as an outer shell (e.g., the processor and/or repository are placed within the outer shell), a transmitter, a receiver, and others.

Figure 18:
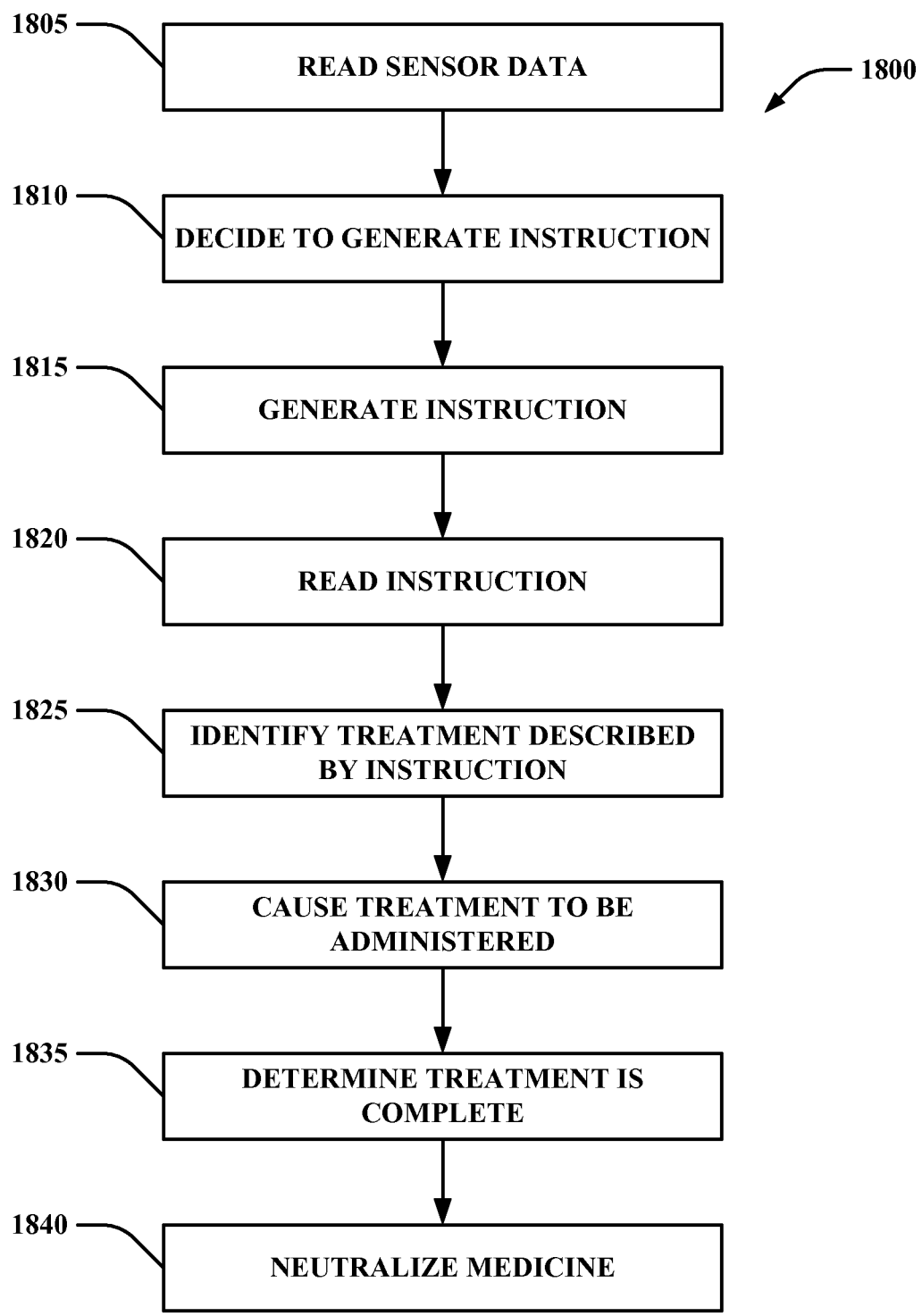

FIG. 18 illustrates one embodiment of a method 1800 for managing treatment. At 1805, sensor data can be read and evaluated. Based on this evaluation, a determination can be made, at 1810, on if an instruction to administer a medical treatment should be generated (e.g. a decision is made to generate an instruction). At 1815, the instruction can be generated and transferred to an apparatus capable of following the instruction.

At 1820, the instruction can be read and, at 1825, a treatment described by the instruction can be identified. In one example, an instruction can state that application penicillin at a certain rate is the treatment. At 1830, the treatment can be caused to be administered (e.g., an instruction is sent to administer the treatment, the treatment is administered, and others). A determination can be made, at 1830, that the treatment is complete (e.g., administration is done, a desired result is achieved, and others) and, at 1835, the medicine can be neutralized into an inert compound.

Figure 19:
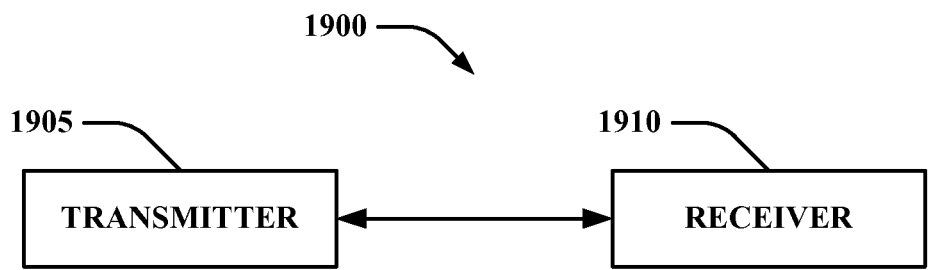

FIG. 19 illustrates one embodiment of a system 1900 that may be used in practicing at least one aspect disclosed herein. The system 1900 includes a transmitter 1905 and a receiver 1910. In one or more embodiments, the transmitter 1905 can include reception capabilities and/or the receiver 1910 can include transmission capabilities. In one embodiment, the system 100 of FIG. 1 includes the transmitter 1905 and/or the receiver 1910. In one example, the receiver 1910 integrates with and/or functions as the collection component 105 of FIG. 1.

The transmitter 1905 and receiver 1910 can each function as a client, a server, and others. The transmitter 1905 and receiver 1910 can each include a computer-readable medium used in operation. The computer-readable medium may include instructions that are executed by the transmitter 1905 or receiver 1910 to cause the transmitter 1905 or receiver to perform a method. The transmitter 1905 and receiver 1910 can engage in a communication with one another. This communication can over a communication medium. Example communication mediums include an intranet, an extranet, the Internet, a secured communication channel, an unsecure communication channel, radio airwaves, a hardwired channel, a wireless channel, and others. Example transmitters 1905 include a base station, a personal computer, a cellular telephone, a personal digital assistant, and others. Example receivers 1910 include a base station, a cellular telephone, personal computer, personal digital assistant, and others. The example system 1900 may function along a Local Access Network (LAN), Wide Area Network (WAN), and others. The aspects described are merely an example of network structures and intended to generally describe, rather than limit, network and/or remote applications of features described herein.

Figure 20:
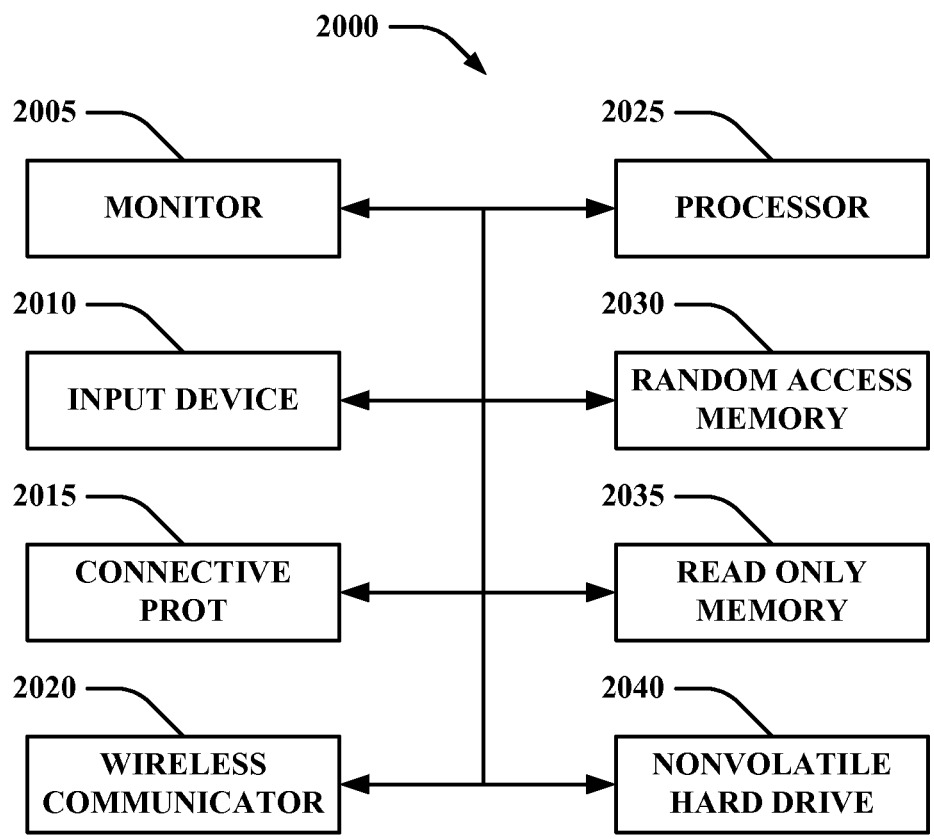

FIG. 20 illustrates one embodiment of a system 2000, upon which at least one aspect disclosed herein can be practiced. In one embodiment, the system 2000 can be considered a computer system that can function in a stand-alone manner as well as communicate with other devices (e.g., a central server, communicate with devices through data network (e.g., Internet) communication, etc.). Information can be displayed through use of a monitor 2005 and a user can provide information through an input device 2010 (e.g., keyboard, mouse, touch screen, etc.). A connective port 2015 can be used to engage the system 2000 with other entities, such as a universal bus port, telephone line, attachment for external hard drive, and the like. Additionally, a wireless communicator 2020 can be employed (e.g., that uses an antenna) to wirelessly engage the system 2000 with another device (e.g., in a secure manner with encryption, over open airwaves, and others). A processor 2025 can be used to execute applications and instructions that relate to the system 2000. In one example, the processor 2025 executes at least one instruction associated with at least one of the collection component 105 of FIG. 1 or the regulation component 110 of FIG. 1. Storage can be used by the system 2000. The storage can be a form of a computer-readable medium. Example storage includes random access memory 2030, read only memory 2035, or nonvolatile hard drive 2040. In one embodiment, the memory 920 of FIG. 9 includes at least one of the random access memory 2030, read only memory 2035, and/or the nonvolatile hard drive 2040.

The system 2000 may run program modules. Program modules can include routines, programs, components, data structures, logic, etc., that perform particular tasks or implement particular abstract data types. The system 2000 can function as a single-processor or multiprocessor computer system, minicomputer, mainframe computer, laptop computer, desktop computer, hand-held computing devices, microprocessor-based or programmable consumer electronics, and the like.

It is to be appreciated that aspects disclosed herein can be practiced through use of artificial intelligence techniques. In one example, a determination or inference described herein can, in one embodiment, be made through use of a Bayesian model, Markov model, statistical projection, neural networks, classifiers (e.g., linear, non-linear, etc.), using provers to analyze logical relationships, rule-based systems, or other technique.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, innovative aspects are not limited to the specific details, the representative apparatus, and illustrative examples shown and described. Thus, this application is intended to embrace alterations, modifications, and variations that fall within the scope of the appended claims.

Functionality described as being performed by one entity (e.g., component, hardware item, and others) may be performed by other entities, and individual aspects can be performed by a plurality of entities simultaneously or otherwise. For example, functionality may be described as being performed by a processor. One skilled in the art will appreciate that this functionality can be performed by different processor types (e.g., a single-core processor, quad-core processor, etc.), different processor quantities (e.g., one processor, two processors, etc.), a processor with other entities (e.g., a processor and storage), a non-processor entity (e.g., mechanical device), and others.

In addition, unless otherwise stated, functionality described as a system may function as part of a method, an apparatus, a method executed by a computer-readable medium, and other embodiments may be implemented in other embodiments. In one example, functionality included in a system may also be part of a method, apparatus, and others.

Where possible, example items may be combined in at least some embodiments. In one example, example items include A, B, C, and others. Thus, possible combinations include A, AB, AC, ABC, AAACCCC, AB, ABCD, and others. Other combinations and permutations are considered in this way, to include a potentially endless number of items or duplicates thereof.

What is claimed is:

1. A system, comprising:
a collection component configured to receive a medical control instruction;
a regulation component configured to control an administration of a treatment to an organism; and
a joiner component configured to combine a medicine with a substance,
where the medical control instruction is based, at least in part, on an organism medical information set for the organism,
where the regulation component is configured to control the administration of the treatment to the organism based, at least in part, on the medical control instruction,
where the administration of the treatment to the organism comprises administering the medicine to the organism,
where combination of the medicine with the substance creates an inert compound,
where the medicine is housed in a first repository,
where the substance is housed in a second repository,
where a housing is configured to retain the first repository,
where the housing is configured to retain the second repository,
where the housing is configured to retain the joiner component,
where the joiner component combines the medicine with the substance,
where the collection component is retained in the housing,
where the regulation component is retained in the housing,
where the housing is orally ingestible by the organism,
where the housing and the components retained by the housing are configured to be dissolved within the organism after the medicine is combined with the substance, and
where a processor executes at least one instruction associated with the collection component, the regulation component, the joiner component, or a combination thereof.

2. A system, comprising:
a repository configured to hold a medicine;
a collection component configured to receive a medical control instruction; and
a release component configured to control, in accordance with the medical control instruction, an amount of the medicine that is dispensed into an organism from the repository,
where the medical control instruction is based, at least in part, on the organism medical information set for the organism,
where an orally ingestible housing retains the repository, the collection component, and the release component, and
where the repository is configured to be physically separated from the orally ingestible housing after the orally ingestible housing exits a gastrointestinal tract of the organism.

3. The system of claim 2, comprising:
a biological sensor configured to produce a sensor data set that pertains to the organism; and
where the sensor data set is generated in view of sensor data that pertains to the organism and
where the orally ingestible housing retains the biological sensor.

4. The system of claim 3, comprising:
a transmitter configured to transmit the sensor data set that pertains to the organism,
where the orally ingestible housing retains the transmitter,
where the transmitter is configured to transmit the sensor data set to a location outside of the organism while the orally ingestible housing is at least partially within the organism,
where a profile of the organism is updated or created in accordance with the sensor data set,
where the collection component is configured to receive the medical control instruction from a location outside of the organism while the orally ingestible housing is at least partially within the organism,
where the release component is configured to control the amount of the medicine while the orally ingestible housing is at least partially within the organism, and
where the biological sensor is configured to produce the sensor data set while the orally ingestible housing is at least partially within the organism.

5. A system, comprising:
a creation component configured to generate a medical control instruction based, at least in part, on a sensor data set produced by a biological sensor and based, at least in part, on an organism medical information set for an organism;
a collection component configured to receive the medical control instruction;
a regulation component configured to control an administration of a treatment to the organism based, at least in part, on the medical control instruction; and
a housing configured to retain the creation component and the collection component.

6. The system of claim 5,
where the regulation component is retained in the housing, and
where the housing is orally ingestible by the organism.

7. The system of claim 6, comprising:
a release component configured to dispense an amount of a medicine,
where the treatment comprises dispensing the amount of the medicine, where the medicine is dispensed from a repository,
where the housing retains the repository, and
where the housing retains the release component.

8. The system of claim 5,
where the biological sensor makes an observation of at least part of a reaction the organism has to a previous treatment,
where the observation produces a medicine reaction data set, and
where the medicine reaction data set is at least part of the sensor data set.

9. The system of claim 8,
where the biological sensor makes an observation of at least part of a reaction the organism has to the treatment
where the creation component is configured to generate a subsequent medical control instruction based, at least in part, on the medicine reaction data set, and
where the regulation component controls administration of a subsequent treatment based, at least in part, on the subsequent medical control instruction.

10. The system of claim 5, comprising:
an evaluation component configured to analyze the sensor data set to produce a sensor data set analysis result; and
a decision component configured to determine if the creation component generates the medical control instruction based, at least in part, on the sensor data set analysis result,
where the creation component generates the medical control instruction in response to a positive determination.

11. The system of claim 5, comprising:
a balance component configured to compare the sensor data set against an organism data set to produce a comparison result,
where the comparison result is used by the creation component to generate the medical control instruction.

12. The system of claim 5, comprising:
a prediction component configured to forecast an expected organism response to the treatment based, at least in part, on the sensor data set and an organism data set,
where the creation component is configured to generate the medical control instruction based, at least in part, on the expected organism response.

13. The system of claim 5,
where the housing is an ingestible housing,
where the ingestible housing retains the regulation component,
where the ingestible housing retains the biological sensor,
where the collection component is configured to function while the ingestible housing is within the organism,
where the regulation component is configured to function while the ingestible housing is within the organism,
where the biological sensor is configured to function while the ingestible housing is within the organism, and
where the creation component is configured to function while the ingestible housing is within the organism.

14. The system of claim 5,
where the organism medical information set comprises a historical characteristic of the organism.

15. The system of claim 5,
where the organism medical information set comprises a classification characteristic of the organism.

16. The system of claim 5, comprising:
a quantity component configured to identify a medication quantity in the organism,
where the creation component is configured to generate the medical control instruction based, at least in part, on the medication quantity.

17. The system of claim 5, comprising:
a component configured to make an observation of the administration of the treatment; and
a component configured to update a community profile based, at least in part, on the observation,
where the organism is represented by the community profile, and
where the community profile represents more than the organism.

18. The system of claim 5, comprising:
an analysis component:
configured to make a determination on an effectiveness of the treatment,
configured to make a determination that an alternative treatment should replace the treatment, and
configured to select the alternative treatment,
where the determination on the effectiveness is based, at least in part, on an observation of the administration of the treatment,
where the determination that the alternative treatment should replace the treatment is based, at least in part, on the effectiveness of the treatment,
where the creation component is configured to generate an alternative medical control instruction that replaces the medical control instruction in response to the selection of the alternative treatment, and
where the regulation component is configured to administer the alternative treatment based, at least in part, on the alternative medical control instruction.

19. The system of claim 18, comprising:
a repository configured to retain a medicine,
where administration of the treatment comprises release of a first quantity of the medicine,
where administration of the alternative treatment comprises release of a second quantity of the medicine,
where the housing is an orally ingestible housing,
where the housing is configured to retain the regulation component, the analysis component, and the repository,
where the creation component is configured to function while the orally ingestible housing travels through a gastrointestinal tract of the organism,
where the collection component is configured to function while the orally ingestible housing travels through the gastrointestinal tract of the organism,
where the regulation component is configured to function while the orally ingestible housing travels through the gastrointestinal tract of the organism, and
where the analysis component is configured to function while the orally ingestible housing travels through the gastrointestinal tract of the organism.

20. The system of claim 5,
where the generation of the medical control instruction by the creation component comprises selection of the medical control instruction and production of the medical control instruction such that the medical control instruction is accessible to the collection component,
where the reception of the medical control instruction by the collection component comprises reading the medical control instruction to produce a reading result, and
where the reading result facilitates control of the administration by the regulation component.

* * * * *